(12) United States Patent
Ascher et al.

(10) Patent No.: US 6,693,095 B2
(45) Date of Patent: Feb. 17, 2004

(54) ANTIBACTERIAL SUBSTITUTED 7-ACYLAMINO-3-(METHYLHYDRAZONO) METHYL-CEPHALOSPORINS AND INTERMEDIATES

(75) Inventors: Gerd Ascher, Kundl (AT); Josef Wieser, Polling (AT); Michael Schranz, Vienna (AT); Johannes Ludescher, Breitenbach (AT); Johannes Hildebrandt, Oeynhausen (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 10/014,651

(22) Filed: Nov. 13, 2001

(65) Prior Publication Data

US 2002/0091252 A1 Jul. 11, 2002

Related U.S. Application Data

(63) Continuation of application No. 09/381,758, filed on Sep. 22, 1999, now abandoned.

(30) Foreign Application Priority Data

Apr. 1, 1997 (AT) ................................................ A547/97

(51) Int. Cl.$^7$ .................... C07D 501/24; A61K 31/546; A61P 31/04
(52) U.S. Cl. ........................................ 514/202; 540/222
(58) Field of Search ........................... 540/222; 514/202

(56) References Cited

U.S. PATENT DOCUMENTS

| | | | |
|---|---|---|---|
| 3,974,153 A | | 8/1976 | Cook et al. |
| 4,327,210 A | | 4/1982 | Montavon et al. |
| 6,440,957 B1 | * | 8/2002 | Ascher et al. .............. 540/222 |
| 2002/0115852 | * | 8/2002 | Ascher et al. .............. 540/222 |

FOREIGN PATENT DOCUMENTS

| | | | |
|---|---|---|---|
| GB | 2 151 617 A | | 7/1985 |
| WO | WO 96/35692 | * | 11/1996 |

OTHER PUBLICATIONS

IMS World Publications Ltd Drug Document for Ceftibuten.*
IMS World Publications Ltd Drug Document for Cefprozil solvate.*
IMS World Publications Ltd Drug Document for Cefatrizine.*
IMS World Publications Ltd Drug Document for Cefadroxil.*
IMS World Publications Ltd Drug Document for Cefiximine.*
IMS World Publications Ltd Drug Document for Ceftriazone.*
IMS World Publications Ltd Drug Document for Ceftazidime.*
Hawley's Condensed Chemical dictionary (Wiley, &Sons) p. 581.*

* cited by examiner

Primary Examiner—Mark L. Berch
(74) Attorney, Agent, or Firm—Gabriel Lopez; Hesna J. Pfeiffer; Peter J. Waibel

(57) ABSTRACT

A compound of formula

I

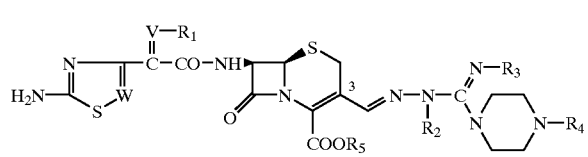

wherein W, V, $R_1$, $R_5$, $R_2$, $R_3$ and $R_4$ have various meanings, a process for their production and their use as a pharmaceutical.

7 Claims, No Drawings

ANTIBACTERIAL SUBSTITUTED 7-ACYLAMINO-3-(METHYLHYDRAZONO) METHYL-CEPHALOSPORINS AND INTERMEDIATES

This is a continuation of application Ser. No. 09/381,758, Sep. 22, 1999, abandoned, which is a 371 of PCT/EP98/01890, Apr. 1, 1998.

The present invention relates to antimicrobial cephalosporins.

In one aspect the present invention provides a compound of formula

I wherein
- $R_1$ denotes hydrogen, acyl, carboxyl, or alkyl;
- $R_2$ and $R_3$ are the same or different and independently of each other denote hydrogen, cycloalkyl, alkyl, alkenyl or alkinyl;
- $R_4$ denotes hydrogen or a group of formula wherein $R_6$ denotes amino, hydrazino, aminoalkylamino, alkoxy, aryl, cycloalkyl, aryloxy, heterocyclyl, alkyl, alkenyl, alkinyl;
- $R_5$ denotes hydrogen or an ester moiety;
- W denotes CH or N;
- V denotes CH or N—O; and
- Z denotes O, S or $NR_7$, wherein $R_7$ is as defined as $R_2$;
with the proviso that not all of $R_2$, $R_3$ and $R_4$ denote hydrogen; and,
if $R_4$ denotes hydrogen, $R_1$ is other than H or $CH_3$.

A compound of formula I includes a compound of formula

Ia wherein W and $R_5$ are as defined above,
- $R'_1$ denotes hydrogen or alkyl, e.g. including unsubstituted alkyl, e.g. $(C_{1-12})$alkyl, such as lower alkyl; or substituted alkyl by e.g. halogen, carboxy; e.g. hydrogen or $CH_2F$;
- $R'_2$ and $R'_3$ are the same or different and independently of each other denote hydrogen; alkenyl; e.g. $(C_{2-4})$ alkenyl; or alkyl;
e.g. unsubstituted or substituted by e.g. halogen, aryl; preferably aryl; including unsubstituted aryl, or aryl substituted by e.g. alkoxy, such as $C_{(1-4)}$alkoxy or hydroxy; e.g.
- $R'_2$ denotes hydrogen, alkyl, or alkenyl; and
- $R'_3$ denotes hydrogen or alkyl; and
- $R'_4$ denotes hydrogen or a group of formula.

wherein
Z' denotes O or $NR'_7$, wherein $R'_7$ denotes hydrogen or alkyl, e.g. lower alkyl; and
$R'_6$ denotes amino, including e.g.(di)lower alkylamino; aminoalkylamino, including e.g ((di)-lower alkyl) amino-(lower)alkylamino; hydrazino; alkoxy, e.g. lower alkoxy; unsubstituted aryl or aryl substituted e.g. by (lower alkyl)carbonyloxy, lower alkoxy; cycloalkyl; a 5 to 6 membered, heterocycle containing 1 to 3 nitrogen and/or sulphur-and/or oxygen atoms, e.g. 1 to 3 nitrogen atoms such as pyrrolidinyl;
alkyl, alkenyl, alkinyl including alkyl, alkenyl, alkinyl interrupted by N, S and/or O; e.g. unsubstituted alkyl, alkenyl, alkinyl or substituted alkyl, alkenyl, alkinyl by hydroxy, aryl, hydroxyaryl, guanidino, nitroguanidino, alkoxy, aryloxy, acyloxy, carbamoyloxy, amino, alkylamino, dialkylamino, trialkylammonium, acylamino, ureido, alkoximino, oximino, imino, carboxy, oxo, halogen, nitro, a carboxylic acid derivative, a sulphonic acid derivative, or heterocyclyl;
such as alkyl, e.g. substituted alkyl, e.g. one or several-fold; by unsubstituted aryl, or substituted aryl by hydroxy, alkoxy, phenoxy; aryloxy, e.g. phenoxy; amino, including e.g. (di)lower alkylamino; hydroxy; carboxy; guanidino or nitroguanidino; or a heterocyclyl-carboximino group; with the proviso that not all of $R_2$, $R_3$ and $R_4$ denote hydrogen.

If not otherwise defined herein any aliphatic group defined herein includes an aliphatic group containing up to 20, e.g. 12, such as 8 C-atoms. Acyl includes aliphatic or aromatic acyl. Lower alkyl includes $(C_{1-4})$alkyl. Aryl includes aryl containing up to 18, e.g. 12 C atoms, including e.g. phenyl, napthyl. Cycloalkyl includes $(C_{3-8})$cycloalkyl, such as $(C_{3-6})$cycloalkyl.

Heterocyclyl includes e.g. saturated or (partially) unsaturated heterocyclyl having 5 or 6 ring members and 1 to 5, e.g. 1 to 3 nitrogen and/or 1 to 3 sulphur and/or oxygen hetero atoms including, for example, condensed heterocyclyl, such as benzthiazolyl. Any group as defined may be unsubstituted or substituted, e.g. by groups which are conventional groups in β-lactam chemistry. Substituted heterocyclyl includes preferably substituted heterocyclyl by amino, hydroxy, alkoxy, acyloxy, carboxy or mercapto. An ester-moiety includes alkyl, preferably $C_{1-6}$alkyl, e.g. $C_{1-4}$alkyl; aralkyl, for example benzyl, alkoxybenzyl, such as 4-methoxybenzyl; indanyl, phthalidyl, alkoxymethyl, e.g. methoxymethyl; $(C_{1-6})$alkanoyloxy$(C_{1-6})$alkyl, $(C_{1-6})$ alkoxy-carbonyl-oxy$(C_{1-6})$alkyl, glycyloxymethyl, phenylglycyloxymethyl, (5-methyl-2-oxo-1,3-dioxolen4-yl)methyl; an ester moiety also includes ester moieties which form with the COO—group a physiologically hydrolysable and acceptable ester, e.g. such known to be hydrolysable ester groups in the field of cephalosporins. A compound of formula I may thus be in the form of an physiologically-hydrolysable and -acceptable ester. By physiologically-hydrolysable and -acceptable esters as used herein is meant an ester in which the COO— group is esterified and which is hydrolysable under physiological conditions to yield an acid which is itself physiologically tolerable at dosages to be administered. The term is thus to be understood as defining regular pro-drug forms. An ester moiety may be preferably a group which is easily hydrolysable under physiological conditions. Such esters may be administered preferably orally. Parenteral administration may be indicated if the ester per se is an active compound or, if hydrolysis occurs in the blood. A silyl group includes a silyl protecting group, e.g. a conventional silyl protecting group, such as a trialkylsilyl group, for example the trimethylsilyl group. A leaving group includes e.g. a leaving group which is conventional in a type of reaction described; in an acylation reaction of an amine group e.g. a carboxylic acid derivative, such as a carboxylic acid halogenide, (active) ester, (mixed) anhydride) may be an appropriate acylation agent. A cation includes a cation which may form a pharmaceutically acceptable salt with a compound of formula I; e.g. a metal salt such as sodium, potassium; or an amine (ammonium) salt, such as trialkylamine, procain, dibenzylamine, benzylamine, ammonium salt.

A compound of formula I includes a compound of formula

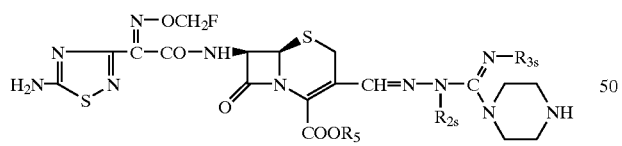

I$_s$ wherein

R$_5$ is as defined above;

R$_{2s}$ and R$_{3s}$ independently of each other denote alkyl, e.g. C$_{1-6}$alkyl, such as lower alkyl; cycloalkyl, aralkyl, e.g. ar(C$_{1-6}$)alkyl, such as ar(C$_{1-4}$)alkyl; aryl; alkenyl, e.g. (C$_{2-6}$)alkenyl, such as (C$_{2-4}$) alkenyl; or alkinyl; and R$_{3s}$ additionally denotes hydrogen; e.g. R$_{2s}$ denotes alkyl, alkenyl or aralkyl; e.g. R$_{3s}$ denotes hydrogen or alkyl; e.g. a compound of formula

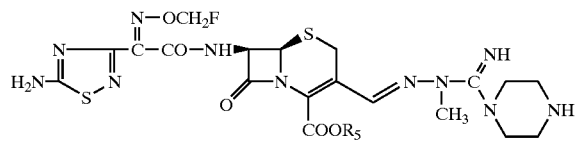

I$_{p1}$ wherein R$_5$ is as defined above.

A compound of formula I includes a compound of formula

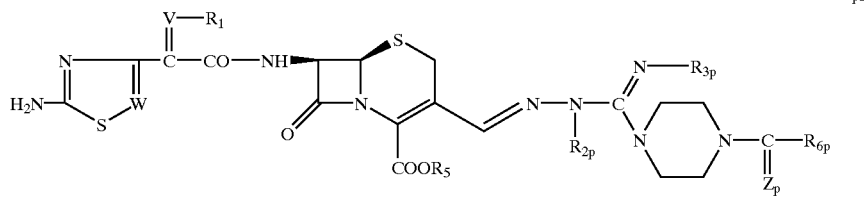

I$_{p2}$ wherein R$_1$, R$_5$, W and V are as defined above,

R$_{2p}$ and R$_{3p}$ are the same or different and independently of each other denote hydrogen, cycloalkyl, or substituted alkyl by halogen or hydroxy, R$_{6p}$ denotes amino, unsubstituted or substituted alkylamino or dialkylamino, alkoxy, aryl, cycloalkyl, aryloxy, an unsubstituted, 5- or 6-membered, saturated, partially saturated or unsaturated heterocycle which may be condensed containing 1 to 5 nitrogen and/or 1 to 3 sulphur- and/or oxygen atoms, a substituted 5- or 6-membered, saturated, partially saturated or unsaturated heterocycle which may be condensed containing 1 to 5 nitrogen and/or 1 to 3 sulphur- and/or oxygen atoms by amino, hydroxy, alkoxy, acyloxy, carboxy or mercapto, cycloalkyl or unsubstituted straight chain or branched (C$_{1-20}$)alkyl, (C$_{1-20}$)alkenyl or (C$_{1-20}$)alkinyl, which may be interrupted by N, S and/or O, once or several times, substituted straight chain or branched (C$_{1-20}$)alkyl, (C$_{1-20}$)alkenyl or (C$_{1-20}$)alkinyl, which may be interrupted by N, S and/or O, by hydroxy, alkoxy, aryloxy, acyloxy, carbamoyloxy, amino, alkylamino, dialkylamino, trialkylammonium, acylamino, ureido, oximino, imino, carboxy, oxo, halogen, nitro, a carboxylic acid derivative, a sulphonic acid derivative, an unsubstituted, 5- or 6-membered, saturated, partially saturated or unsaturated heterocycle containing 1 to 5 nitrogen and/or 1 to 3 sulphur- and/or oxygen atoms which may be condensed; or a substituted 5- or 6-membered, saturated, partially saturated or unsaturated heterocycle which may be condensed containing 1 to 5 nitrogen and/or 1 to 3 sulphur- and/or oxygen atoms by amino, hydroxy, alkoxy, acyloxy, carboxy or mercapto;

Z$_p$ denotes oxygen or NR$_{7p}$, wherein R$_{7p}$ is as defined R$_{2p}$.-

A compound of formula I includes a compound of formula

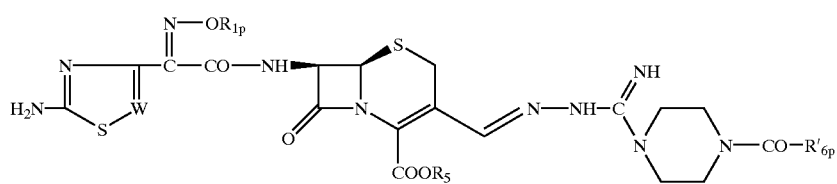

wherein W and $R_5$ are as defined above,
$R_{1p}$ denotes hydrogen or $CH_2F$, and
$R'_{6p}$ denotes hydrogen, $(C_{1-20})$alkyl, one or two fold substituted $(C_{1-20})$alkyl by phenyl, phenoxy, amino, hydroxyphenyl, hydroxy, carboxyl, guanidino or nitroguanidino, unsubstituted phenyl or substituted phenyl by acetoxy, pyrrolidinyl; or a compound of formula

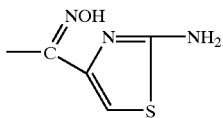

A compound of formulae I includes a compound of formulae Ia, Is, $I_{p1}$, $I_{p2}$, and $I_{p3}$ and may be e.g. in free form and in the form of a salt and/or in the form of a solvate. A salt includes any possible salt, e.g. an acid addition salt; such as a hydrochloride, internal salt, metal salt, quaternary salt and an amine salt of a compound of formula I. Metal salts include for example sodium, potassium, calcium, barium, zinc, aluminum salts, preferably sodium or potassium salts. Amine salts include for example trialkylamine, procaine, dibenzylamine and benzylamine salts. A salt may preferably be a pharmaceutically acceptable salt of a compound of formula I.

A solvate includes a solvate with an organic solvent and a solvate with water, such as a hydrate.

A compound of formula I may be e.g. in the form of a hydrochloride, such as a monohydrochloride, dihydrochloride, trihydrochloride, e.g. in crystalline form and/or in the form of a solvate, e.g. a hydrate.

A free form of a compound of formula I may be converted into a salt form and vice versa. A solvate form of a compound of formula I, e.g. in free form or in the form of a salt, may be converted in a non-solvate form and vice versa.

A compound of formula I includes a compound of formula I in any configuration, e.g. in any possible stereoisomeric form. Mixtures of stereoisomeric forms may be separated, e.g. as conventional, e.g. by chromatography,

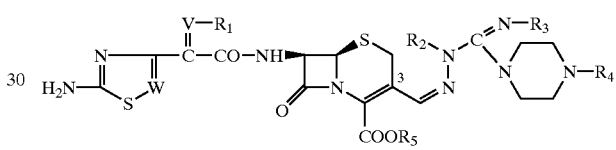

fractioned crystallisation. E.g. the configuration of $R_1$ in group $—C{=}VR_1$ may be syn [(Z)] and anti [(E)] and is preferably, e.g. predominantly, syn [(Z)]; e.g. containing the [(E)] form in an amount of 0 to 5%, e.g. 0 to 2%.

A compound of formula I may be in the form of a mixture of the 3(E)-form and 3-(Z)-form, or may be, e.g. predominantly, in the 3(Z)-form, e.g. according to formula

I(Z)

(structure)

or may be, e.g. predominantly, in the 3(E)-form, e.g. according to formula

I(E)

(structure)

wherein $R_1$ and $R_2$ are as defined above, and wherein the configuration of the group

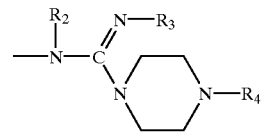

attached to the nitrogen of the $—C{=}N$ group in position 3 of the ring system is, e.g. 3(E) and/or 3(Z). A compound of formula I may be, e.g. predominantly, in the 3(E)-form, e.g. containing the 3(Z)-form in an amount of 0 to 5%, e.g. 0 to 2% or predominantly in the 3(Z)-form, e.g. containing the 3(Z)-form in an amount of 0 to 5%, e.g. 0 to 2%. A compound of formulae Is and $I_{p1}$ may be, e.g. predominantly, in the 3(E)-form, e.g. containing the 3(Z)-form in an amount of 0 to 5%, e.g. 0 to 2%.

A compound of formula I may be obtained as follows:

a) Reacting a compound of formula

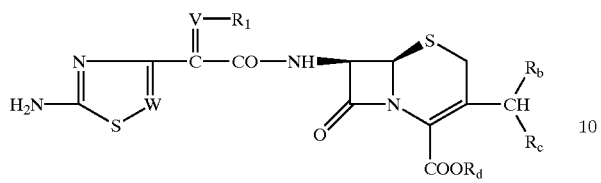

II wherein W, V and $R_1$ are as defined above and wherein

α) $R_b$ denotes hydroxy and $R_c$ and $R_d$ together denote a bond, or

β) $R_d$ denotes hydrogen, a cation, an ester moiety or a silyl group and $R_b$ and $R_c$ denote the oxo group e.g. in free form or in the form of an acid addition salt, with a compound of formula

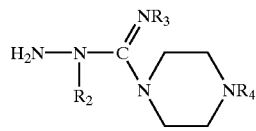

III wherein $R_2$, $R_3$ and $R_4$ are as defined above, e.g. in free form or in the form of an acid addition salt, e.g. as appropriate, e.g. as conventional b) for the production of a compound of formula

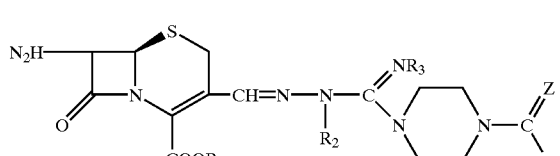

IV wherein W, V, Z, $R_1$, $R_2$, $R_3$, $R_5$ and $R_6$ are as defined above, acylating a compound of formula wherein Z, $R_2$, $R_3$, $R_5$ and $R_6$ are as defined above, e.g. in free form or in the form of an acid addition salt, e.g. as appropriate, e.g. as conventional with a compound of formula

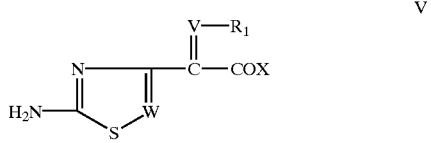

V wherein V, W and $R_1$, are as defined above and X denotes a leaving group, e.g. in free form or in the form of an acid addition salt; e.g. as appropriate, e.g. as conventional; or reacting a compound of formula

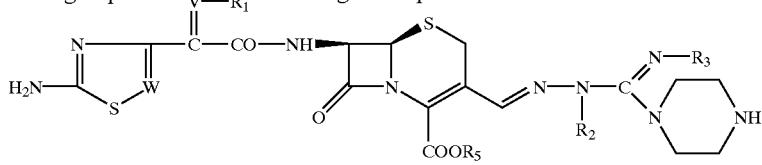

wherein $R_1$, $R_2$, $R_3$, $R_5$, V and W are as defined above, e.g. in free form or in the form of an acid addition salt, e.g. as appropriate, e.g. as conventional with a compound of formula

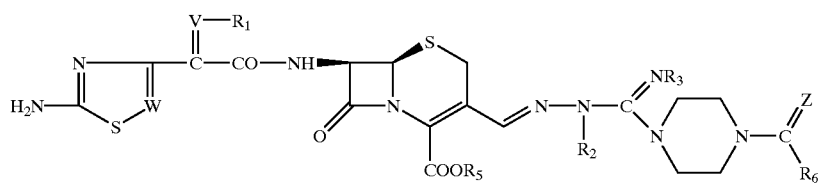

Va wherein $R_6$ and Z are as defined above and X denotes a leaving group.

Reactive groups in a compound of of formulae I, Ib, Ic, II, III, IV, V and Va may be protected by protecting groups, e.g. protecting groups which are conventional, e.g. in cephalosporin chemistry. Silyl protecting group technology in the Ib presence of a solvent which may be inert towards silylation agents, e.g. a chlorinated hydrocarbon, such as dichloromethane; a nitrile such as acetonitrile, an ether such as tetrahydrofuran, a dipolar aprotic solvent, e.g. N,N-dimethylformamide; or a solvent system, e.g. mixtures of individual solvents, e.g. as described above; may be appropriate for the protection of reactive groups. Protecting groups may be split off, e.g. as conventional during a corresponding reaction or after termination of a corresponding reaction. A compound of formula I wherein $R_5$ denotes hydrogen may be converted into a compound of formula I wherein $R_5$ denotes an ester moiety or vice versa. A compound of formula I may be isolated from the reaction mixture, e.g. as conventional. A compound of formula I may be obtained in free form or in the form of a salt and/or a hydrate. A compound of formula I in free form may be converted into a compound of formula in the form of a salt and/or a hydrate and vice versa.

Process a) may be carried out as follows:

A compound of formula II may be reacted with a compound of formula III, e.g. in a solvent, e.g. in a solvent which is inert under the reaction conditions, such as water; a mixture of water with an e.g. lower, e.g. ($C_{1-4}$)alcohol or dioxane; or in a dipolar aprotic solvent, e.g. dimethylformamide, dimethylsulfoxide, dimethylacetamide, if desired in mixture with an alcohol and/or water; at temperatures from −20 to 50° C. The pH may be at an optimum, e.g. by addition of an organic or inorganic acid or base. A compound of formula I obtained may be isolated and/or purified, e.g. as conventional, e.g. by addition of an anti-solvent or by chromatography.

Process b) may be carried out e.g. as conventional for an acylation reaction. E.g. a compound of formula IV may be reacted with a compound of formula V; or a compound of formula Ic may be reacted with a compound of formula Va; e.g. in an appropriate solvent, such as a mixture of water and acetone or acetonitrile at appropriate temperatures, e.g. at room temperature.

Starting compounds are known or may be produced according to known, e.g. analogous methods, or e.g. according to the present examples. A part of the starting compounds according to the present invention is novel.

In another aspect the present invention provides a compound selected from
1-[(1-Methylhydrazino)iminomethyl]piperazine
1-[(1-Ethylhydrazino)iminomethyl]piperazine
1-[(1-Allylhydrazino)iminomethyl]piperazine
1-[(1-(4-Methoxybenzyl)hydrazino]iminomethyl]piperazine
1-[(1-(4-Methoxybenzyl)hydrazino]iminomethyl]piperazine
1-[(1-(3,4,5-Trimethoxybenzyl)hydrazino]iminomethyl]piperazine
1-[(1-Methylhydrazino)(methylimino)methyl]piperazine
Glycin-(4-hydrazinoiminomethyl)piperazide
1-(R)-(Amino(4-hydroxyphenyl)acetyl)4-(hydrazinoiminomethyl)piperazine
1,4-bis-(Hydrazinoiminomethyl)piperazine
1-(Hydrazinoiminomethyl)4-[ethyfimino)[3-dimethylaminopropyl)amino]methyl]piperazine, e.g. in the form of a salt, such as a hydrochloride, and/or in the form of a solvate; and, in another aspect, a compound of formula

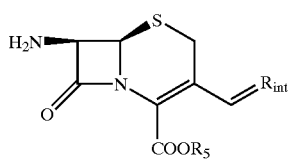

$I_{int}$ wherein $R_5$ is as defined in claim 1, and $R_{int}$ denotes a group

which is formed by a bond of the terminal amine group of the hydrazino group of a compound selected from the list above and wherein the —N— group is substituted according to a compound selected from the list above, i.e. a hydrazino-compound listed above is bond to the ring system via the terminal amine group of the hydrazino group to the methyl group in position 3 of the ring system to form a group

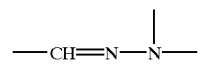

wherein the —N— group is substituted according to a hydrazino compound listed above.

The compounds of formulae I, hereinafter designated as "active compound(s)) of the invention" exhibits pharmacological activity and surprising low toxicity and are therefore useful as pharmaceuticals. In particular, the active compounds of the invention show antimicrobial, e.g. antibacterial, activity against aerobic and anaerobic growing bacteria, e.g. gram negative and gram positive bacteria such as Enterobacter, e.g. *Enterobacter cloacae;* Enterococcus, e.g. *Enterococcus faecalis, Enterococcus faecium;* Moraxella, e.g. *Moraxella catarrhalis;* Haemophilus, e.g. *Haemophilus influenza;* Klebsiella, e.g. *Klebsiella edwardsii, Klebsiella pneumoniae;* Streptococcus, e.g. *Streptococcus pyogenes;* Staphylococcus, e.g. *Staphylococcus aureus* MSSA (methicillin sensitive strains); *Staphylococcus aureus* MRSA (methicillin resistant strains); Escherichia, e.g. *Escherichia coli;* Proteus, e.g. *Proteus mirabilis,* Salmonella, e.g. *Salmonella typhimurium,* Serratia, e.g. *Serratia marcescens,* Pseudomonas, e.g. *Pseudomonas aeruginosa;* Pneumococci, e.g. *Pneumococcus pneumoniae* (penicillin sensitive and mult-drug resistant strains); in vitro in the Agar DilutionTest for bacteria according to National Commitee for Clinical Laboratory Standards (NCCLS) 1993, Document-M7-A3 Vol.13, No. 25: "Methods for dilution Antimicrobial Susceptibility Tests for Bacteria that Grow Aerobically-Third Edition, Approved Standard"; and Document M11-A3 for anaerobic bacteria
in a concentration from about 0.001 to ca. 50 μg/ml (MIC), e.g. using strains including *Staphylococcus aureus* (ATCC 29213 and ATCC 9144); *Enterococcus faecalis* (ATCC 29212); *Haemophilus influenza* (NTCC 49247 and NCTC 11931); *Escherichia coli* (ATCC 25922 and ATCC 35218); *Klebsiella pneumoniae* (NCTC 11228); *Klebsiella edwardsii* (NCTC 10896); *Pseudomonas aeruginosa* (ATCC 27853 and ATCC 25668); and in vivo in the septicaemia mouse model, in accordance to the method description Nr. 159 A-5, approved by Austrian Health Authorities (MA 58, no. 2968/95 of 12-Oct-1995), e.g. when administerd at dosages from about 0.05 to 50 mg/kg body weight, such as 0.1 to 50 mg/kg body weight ($ED_{50}$ values). E.g., mice are infected with an ED 95% of *Staphylococcus aureus* (ATCC 4995), *Streprococcus pyogenes* (ATCC 29218), *Escherichia coli* (Δ 12 NFI culture collection) and are treated 1, 5 and 24 hours after infection. The ED 50% values ranging from ca. 0.2 to 50 mg/kg body weight are calculated by Probit analysis of the administered dosages of compounds. Activity is determined by numbers of surviving animals per group of 8 mice per dosage until day 5 after infection.

The active compounds of the invention show an surprising overall activity spectrum. It has, for example, been determined that the MHK (μg/ml) of the compound of Example 1 against, for example *Enterococcus faecalis* is of ca. 0.1 to 0.4; against *Staphylococcus aureus* (MSSA) is of ca. <0.125 to 0.8; against methicillin resistant *Staphyloccous aureus* is of 0.8 to 6.4; against multi-drug resistant Pneumococcus is of 0.4.

The active compounds of the invention are therefore useful for the treatment of microbial, e.g. bacterial diseases.

For this indication, the appropriate dosage will, of course, vary depending upon, for example, the compound of formula I employed, the host, the mode of administration and the nature and severity of the conditions being treated.

However, in general, for satisfactory results in larger mammals, for example humans, an indicated daily dosage is in the range from about 0.05 to 5 g, for example 0.1 to about 2.5 g, of an active compound of the invention conveniently administered, for example, in divided doses up to four times a day.

An active compound of the invention may be administered by any conventional route, for example orally, e.g. in the form of tablets or capsules, or parenterally in the form of injectable solutions or suspensions, e.g. in analogous manner to cefotaxime.

The compound 7-(((5-amino-1,2,4-thiadiazol-3-yl)-(Z)-(fluormethoxyimino)acetyl)amino)-3-((imino-1-piperazinylmethyl)methylhydrazono)methyl-3-cephem4-carboxylic acid (compound of Example 1) is the preferred compound of the invention for use as an antimicrobial agent. It has, for example been determined that the MHK ($\mu$g/ml) of the compound of Example 1 (tested in the form of the hydrochloride) against, for example *Haemophilus influenza* is ca. <0.125 to 0.4 and, for example cefotaxime shows an MHK ($\mu$g/ml) of ca. <0.125 to 0.4. It is therefore, indicated that for the treatment of microbial diseases, e.g. bacterial diseases the preferred compounds of the invention may be administered to larger mammals, for example humans, by similar modes of administration at similar dosages than conventionally employed with cefotaxime.

A compound of formula I may be administered in the form of a pharmaceutically acceptable salt, e.g. an acid addition salt or a base addition salt or in the corresponding free form, if desired in the form of a solvate. Such a saltisolvate may exhibit the same order of activity as the free form.

The present invention also provides a pharmaceutical composition comprising a compound of formula I according to claim 1 in the form of a pharmaceutically acceptable salt or in free form in association with at least one pharmaceutical carrier or diluent.

Such compositions may be manufactured in conventional manner. Unit dosage form may contain, for example 10 mg to about 1 g, for example 10 mg to about 700 mg, such as to about 500 mg.

As medicaments, the active ingredients according to the invention may be administered alone or in suitable medicinal forms together with inorganic or organic, pharmacologically inert excipients. For example, they are used as a constituent of capsules, or injection or instillation preparations, which contain a quantity of active compounds that is sufficient to attain an optimum blood level, that is, ca. 10 to 500 mg per capsule. For this application, the dosage to be administered depends on the compound used and the type of administration, as well as the type of treatment. With larger mammals, satisfactory results may be obtained when administering a daily dose of ca. 0.5 to 6 g. If required, this amount may be given in correspondingly smaller doses two to four times daily, or in sustained release form.

In another aspect the present invention provides a compound of formula I or a composition comprising a compound of formula I in the form of a pharmaceutically acceptable salt or in free form in association with at least one pharmaceutical carrier or diluent for use as a pharmaceutical, e.g. as an antibiotic; and The use of a compound of formula I, or use of a composition comprising a compound of formula I in the form of a pharmaceutically acceptable salt or in free form in association with at least one pharmaceutical carrier or diluent as a pharmaceutical.

In a further aspect the present invention provides a method of treatment of microbial diseases, e.g. caused by bacterias selected from Pseudomonas, Enterobacter, Enterococcus, Moraxella, Haemophilus, Klebsiella, Streptococcus, Staphylococcus, Escherichia, Proteus, Salmonella, Serratia or Pneumococci, which comprises administering to a subject in need of such treatment, an effective amount of a compound of formula I; e.g. in the form of a pharmaceutical composition according to the present invention; and A compound of formula I for use in the preparation of a medicament for the treatment of microbial diseases, for example of diseaeses caused by bacterias selected from Pseudomonas, Enterobacter, Enterococcus, Moraxella, Haemophilus, Klebsiella, Streptococcus, Staphylococcus, Escherichia, Proteus, Salmonella, Serratia or Pneumococci.

In the following examples, which illustrate the invention more fully but should in no way limit its scope, all temperatures are given in degrees Celsius. $^1$H-NMR: 200 MHz, DMSO-d$_6$.

EXAMPLE 1

7-(((5-amino-1,2,4-thiadiazol-3-yl)-(Z)-(fluoromethoxyimino)acetyl)amino)-3-(imino-1-piperazinyhmethyl)medtylhydrazono)methyl-3-cephem4-carboxylic acid a) N-(1,4,5a,6-tetrahydro-3-hydroxy-1,7-dioxo-3H,7H-aceto(2,1-b)furo(3,4-d) (1,3)-thiazin-6-yl)-2-(5-amino-1,2,4-thiadiazol-3-yl)-(Z)-2-fluoromethoxyimino)acetic acid amide (hydroxylactone of 7-(((5-amino-1,2,4-thiadiazol-3-yl)-(Z)-(fluoromethoxyimino)acetyl) amino)-3-formyl-3-cephem-4-carboxylic Acid)

A suspension of 10 g of 7-amino-3-formyl-3-cephem4-carboxylic acid in a mixture of 220 ml of methylene chloride and 80 ml of acetonitrile is stirred at 0° with 43 ml of N,O-bis(trimethylsilyl)-acetamide. 15.7 g of (5-amino-1,2,4-thiadiazol-3-yl)-(Z)-2-fluoromethoxyimino-acetic acid chloride are added to the clear solution obtained and the reaction mixture is stirred for ca. one hour at ca. 0°. The mixture is diluted with 1250 ml of acetonitrile which contains 70 ml of water. 12% aqueous ammonia is added to the mixture obtained to adjust a pH value of 3.5. The mixture is diluted with 2.5 litres of water and extracted with ethyl acetate. The ethyl acetate phase is dried and concentrated. The concentrate is stirred for one hour at 20° with 100 ml of acetonitrile. N-(1,4,5a,6-tetrahydro-3-hydroxy-1,7-dioxo-3H,7H-aceto(2,1-b)furo(3,4-d)(1,3)-thiazin-6-yl)-2-thiadiazol-3-yl)-(Z)-2-(fluoromethoxyimino)acetic acid amide precipitates in crytalline form, is filtrated off and dried.

b) 7-(((5-amino-1,2,4-thiadiazol-3-yl)-(Z)-fluoromethoxyimino)acetyl)amino)-3(E)-(imino-1-piperazinylmethyl)methylhydrazono)methyl-3-cephem4-carboxylic Acid 3.77 g of N-(1,4,5a,6-tetrahydro-3-hydroxy-1,7-dioxo-3H,7H-aceto(2,1-b) furo(3,4-d)(1,3)-thiazin-6-yl)-2-(5-amino-1,2,4-thiadiazol-3-yl)-(Z)-2-fluoromethoxyimino) acetic acid amide are suspended in a mixture of 75 ml of acetonitrile and 11 ml of water and treated with a solution of 2 g of 1-(1-methylhydrazino)iminomethyl)piperazine in the form of a dihydro-chloride in 4.5 ml of 2N HCl. The reaction mixture is stirred for ca. one day at room temperature and poured into 600 ml of acetonitrile under stirring. 7-(((5-amino-1,2,4-thiadiazol-3-yl)-(Z)-(fluoromethoxy-imino)acetyl)amino)-3(E)-(imino-1-piperazinylmethyl)-methylhydrazono)methyl-3-cephem-4-carboxylic acid in the form of a trihydrochloride precipitates, is filtrated off, washed with acetonitrile and dried.

c) 7-(((5-amino-1,2,4-thiadiazol-3-yl)-(Z)-(fluoromethoyimino)accetyl)amino)-3(E)-(imino-1-piperazinylmethyl)methylhydrazono)methyl-3-cephem4-carboxylic Acid 0.65 g of crude 7-(((5-amino-1,2,4-thiadiazol-3-yl)-(Z)-(fluoromethoxy-imino)acetyl) amino)-3(E)-(imino-1-piperazinylmethyl)methylhydrazono)methyl-3-cephem-4-carboxylic acid in the form of a trihydrochloride obtained in step b) are dissolved in 2 ml of water and filled into a column which is filled with 50 g of RP-18$^R$ (LiChroprep RP-18$^R$, grain size 40–63 μm, Merck) and eluated with water (flow rate 20 ml/min). Fractions are examined by means of analytical HPLC and the fractions which contain 7-(((5-amino-1,2,4-thiadiazol-3-yl)-(Z)-(fluorometh-oxymino) acetyl)-amino)-3(E)-(imino-1-piperazinylmethyl) methylhydrazono)methyl-3-cephem-4-carboxylic acid in the form of a monohydrochlorid are determined (HPLC), combined and lyophilised.

In the manner described in Example 1 but using corresponding compounds of formulae II and III wherein W, V, $R_1$, $R_2$, $R_3$, $R_4$ and $R_5$ have the meaning given in TABLE 1 below, compounds of formula I, wherein W=N, V=N—O, $R_4$=$R_5$=H and $R_1$=$CH_2F$ and $R_2$ and $R_3$ have the meaning listed in TABLE 1 below are obtained, e.g. in the salt form described:

TABLE 1

| Ex. | $R_2$ | $R_3$ | Salt |
|---|---|---|---|
| 2 | $C_2H_5$ | H | HCl |
| 3 | $CH_3$ | $C_2H_5$ | HCl |
| 4 | —$CH_2CH$=$CH_2$ | H | 3HCl |
| 5 | $CH_3$ | $CH_3$ | HCl |
| 6 | —$CH_2$—C$_6$H$_4$—$OCH_3$ | H | 3HCl |
| 7 | —$CH_2$—C$_6$H$_3$($OCH_3$)($OCH_3$)($OCH_3$) | H | 3HCl |

EXAMPLE 8

6R-(6a,7β(Z))-7-[2-(2-aminothiazol4-yl)-2-hydroxyininoacetylamino]-3-[[(imino-4-(ethoxycarbonyl)piperazin-1-ylmethyl)hydrazono] methyl]-3-cephem4-carboxylic Acid 5.2 g of N,O-bistrimethylsilyl acetamide are added dropwise whilst stirring to a suspension of 1 g 6R-(6a,7b(Z))-7-[2-(2-aminothiazol4-yl)-2-hydroxyiminoaceryl-amino]-3-[[(imino-1-piperazinylmethyl)hydrazono]methyl]-3-cephem-4-carboxylic acid in the form of a trihydro-cloride in a mixture of 50 ml of absolute methylene chloride and 50 ml of absolute acetonitrile. To the clear solution obtained 0.28 g of chloroformic acid ethyl ester are added dropwise whilst stirring. The mixture is stirred for ca. 20 minutes at room temperature and treated with 0.95 g of water. 6R-(6a,7b(Z))-7-[2-(2-aminothiazol4-yl)-2-hydroxyiminoacetyl-amino]-3-[[(imino4-(ethoxycarbonyl)piperazin-1-ylmethyl) hydrazono]methyl]-3-cephem4-carboxylic acid in the form of a dihydrochloride precipitates, is filtrated off, washed and dried.

EXAMPLE 9

6R-(6a,7β(Z))-7-[2-(2-aminothiazol4-yl)2-hydroxyiminoacetylamino]-3-[[(imino-4-(aminoacetyl) piperazin-1-ylmethyl)hydrazono] methyl]-3-cephem-4-carboxylic Acid 0.6 g of glycine-(4-hydrazinoiminomethyl)piperazide in the form of a dihydrochloride are added in one portion to a solution of 0.6 g of N-(1,4,5a,6-tetrahydro-3-hydroxy-1,7-dioxo-3H,7H-aceto[2,1-b]furo[3,4-d][1,3]thiazin-6-yl)-2-(2-aminothiazol-4-yl)-(Z)-2(hydroxy-imino) acetic acid amide in a mixture of 10.7 ml of acetonitrile, 3.6 ml of water and 0.7 ml of 8 N HCl, and the reaction mixture obtained is stirred at room temperature. 6R-(6a,7β(Z))-7-[2-(2-aminothiazol4-yl)-2-hydroxyiminoacetylanidno]-3-[[(imino4-(aminoacetyl) piperazin-1-ylmethyl)hydrazono] methyl]-3-cephem-4-carboxylic acid in the form of a trihydrochloride precipitates within 2 hours whilst stirring, is filtrated off, washed and dried.

In the manner as described in Examples 8 and 9 but using corresponding compounds of formulae II and III wherein W, V, $R_1$, $R_2$, $R_3$, $R_4$ and $R_5$ have the meaning given in TABLE 2 below, compounds of formula I, wherein V=N—O, $R_2$=$R_3$=$R_5$=H and W, $R_1$ and $R_4$ have the meaning listed in TABLE 1 below are obtained, e.g. in the salt form described:

TABLE 2

| Example | W | $R_1$ | $R_4$ | Salt |
|---|---|---|---|---|
| 10 | CH | H | —CO—C$_6$H$_5$ | 2HCl |
| 11 | CH | H | —$COCH_3$ | 2HCl |
| 12 | CH | H | —CO—$CH_2$—C$_6$H$_5$ | 2HCl |
| 13 | CH | H | —CO—C(=NOH)—(2-aminothiazol-4-yl) | 3HCl |

TABLE 2-continued

| Example | W | R₁ | R₄ | Salt |
|---|---|---|---|---|
| 14 | CH | H | —CO—N(CH₃)₂ | 2HCl |
| 15 | CH | H | —CO—CH₂—O—C₆H₅ | 2HCl |
| 16 | CH | H | —CO(S)—(2-pyrrolidinyl) | 3HCl |
| 17 | CH | H | —CO—(2-OCOCH₃-C₆H₄) | 2HCl |
| 18 | CH | H | —CO—CH(R)(NH₂)—C₆H₅ | 3HCl |
| 19 | CH | H | —CO—CH(R)(NH₂)—C₆H₄—OH | 3HCl |
| 20 | CH | H | —CO—CH(S)(NH₂)—(CH₂)₃—NH—C(=NH)—NH—NO₂ | 3HCl |
| 21 | CH | H | —CO—CH₂OH | 2HCl |
| 22 | CH | H | —CO—CH(S)(NH₂)—(CH₂)₃—NH—C(=NH)—NH₂ | 4HCl |
| 23 | CH | H | —CO—CH(S)(NH₂)—(CH₂)₂—COOH | 2HCl |
| 24 | CH | H | —CO—CH(S)(NH₂)—CH(S)(CH₃)—C₂H₅ | 3HCl |
| 25 | CH | H | —CO—(CH₂)₅—CH₃ | 2HCl |
| 26 | CH | H | —CO—(CH₂)₁₆—CH₃ | 2HCl |
| 27 | CH | H | —CO—(CH₂)₁₄—CH₃ | 2HCl |
| 28 | CH | H | —CO—(CH₂)₆—CH₃ | 2HCl |
| 29 | CH | H | —CO—CH(OH)—CH₂OH | 2HCl |
| 30 | N | CH₂—F | —CO—CH₂—O—C₆H₅ | 2HCl |
| 31 | N | CH₂—F | —CO—(2-OCOCH₃-C₆H₄) | 2HCl |

TABLE 2-continued

| Example | W | R₁ | R₄ | Salt |
|---|---|---|---|---|
| 32 | N | CH₂—F | —CO—CH₃ | 2HCl |
| 33 | N | CH₂—F | —CO—(S)-pyrrolidin-2-yl (NH) | 3HCl |
| 34 | N | CH₂—F | —CO—CH₂—NH₂ | 3HCl |
| 35 | N | CH₂—F | —CO—CH(S)(NH₂)—CH(S)(CH₃)—C₂H₅ | 3HCl |
| 36 | N | CH₂—F | —CO—CH(R)(NH₂)—C₆H₄—OH | 3HCl |
| 37 | N | CH₂—F | —C(=NH)—NH—NH₂ | 3HCl |
| 38 | N | CH₂—F | —C(=N—C₂H₅)—NH—(CH₂)₃—N(CH₃)₂ | 3HCl |
| 39 | CH | H | —C(=NH)—NH—NH₂ | 3HCl |
| 40 | CH | H | —CO—(CH₂)₂—COOH | 2HCl |
| 41 | CH | H | —CO—cyclopropyl | 2HCl |
| 42 | CH | H | —CO—(3,4,5-trimethoxyphenyl) | 2HCl |
| 43 | N | CH₂—F | —CO—(3,4,5-trimethoxyphenyl) | 2HCl |
| 44 | CH | H | —CO—CH(S)(CH₃)—NH₂ | 3HCl |
| 45 | CH | H | —CO—CH(R)(CH₃)—NH₂ | 3HCl |

EXAMPLE 46

[6(R)-6a,7β(Z)]-7-[[(5-amino-1,2,4-thiadiazol-3-yl)-(fluoromethoxyimino)-acetyl]amino]3-[(imino-4-acetylpiperazin-1-ylmethyl)hydrazonomethyl]-3-cephem-4-carboxylic acid-1-(isopropoxycarbonyloxy)ethylester 1.5 g of [6(R)-6a,7β(Z)]-7-[[(5-amino-1,2,4-thiadiazol-3-yl)-(fluoromethoxyimino)acetyl]-amino]-3-[(iminopiperazine-1-ylmethyl)hydrazonomethyl]-3-cephem-4-carboxylic acid-1-(isopropoxycarbonyloxy)ethylester in the form of a dihydrochloride (mixture of two diastereoisomers in a ration of 1:1) precipitates, is filtrated off, washed and dried.

In the manner described in Example 47 but using corresponding starting compounds of formulae II and III wherein W, V, $R_1$, $R_2$, $R_3$, $R_4$ and $R_5$ have the meaning given in TABLE 3 below, compounds of formula I, wherein W=N, V=N—O, $R_1$=CH$_2$F, $R_2$=$R_3$=H and $R_4$ and $R_5$ are as listed in TABLE 3 below are obtained:

TABLE 3

| Example | R$_4$ | R$_5$ |
|---|---|---|
| 48 | —CO—CH(R)(NH$_2$)—C$_6$H$_4$—OH | —CH(CH$_3$)—OCOOCH(CH$_3$)$_2$ |
| 49 | —CO—CH(R)(NH$_2$)—C$_6$H$_4$—OH | —CH$_2$—OCOC(CH$_3$)$_3$ |
| 50 | H | —CH$_2$—OCOC(CH$_3$)$_3$ | cephem4-carboxylic acid-1-(isopropoxycarbonyloxy) ethylester in the form of a dihydrochloride are stirred at 0° in a mixture of 30 ml of methylene chloride, 10 ml of acetonitrile and 15 ml of dimethylformamide with 2.2 ml of N,O-bistrimethylsilyl acetamide. To the clear solution obtained 160 ml of acetyl chloride are added, stirring is continued for ca. 60 minutes at 0°. The reaction mixture is introduced into 100 ml of water. The pH of the mixture obtained is adjusted to 7 by addition of 0.5 N sodium bicarbonate solution and the mixture obtained is extracted with ethyl acetate. The ethyl acetate phase is washed with water, dried over sodium sulphate and the solvent is evaporated off. The residue is treated with ether. [6(R)-6a,7β(Z)]-7-[[(5-Amino-1,2,4-thiadiazol-3-yl)-(fluoromethoxyimino)-aceryl]amino]3-[(imino4-acetylpiperazin-1-ylmethyl) hydrazonomethyl]-3-cephem4-carboxylic acid-1-(isopropoxycarbonyloxy)ethylester (mixture of two diastereoisomers in a ration of 1:1) precipitates, is filtrated off and dried.

EXAMPLE 47

[6(R)-6α,7β(Z)]-7-[[(5-Amino-1,2,4-thiadiazol-3-yl)-(fluormethoxyimino) acetyl]amino]-3-[(iminopiperazin-1-ylmethyl)hydrazonomethyl]-3-cephem-4-carboxylic acid-1-(isopropoxycarbonyloxy)ethylester 3.1 g of [6(R)-6α,7β(Z))-7-[[(5-Amino-1,2,4-thiadiazol-3-yl)-(fluormethoxyimino)acetyl]-amino]-3-formyl-3-cephem-4-carboxylic acid-1-(isopropoxycarbonyloxy) ethylester in 30 ml of acetonitrile are treated with a solution of 1.11 g of 1-(hydrazinoimino-methyl)piperazine in the form of a dihydrochloride in 2.5 ml of 2 N hydrochloric acid. The mixture is stirred for ca. 1 hour and introduced into 300 ml of acetonitrile. [6(R)-6α,7β(Z))-7-[[(5-Amino-1,2,4-thiadiazol-3-yl)-(fluormethoxyimino) acetyl]amino]-3-[(iminopiperazin-1-ylmethyl) hydrazono-methyl]-3-cephem-4-carboxylic acid-1-(isopropoxycarbonyloxy) ethylester in the form of a dihydrochloride (mixture of two diastereoisomers in a ration of 1:1) precipitates, is filtrated off, washed and dried.

Compounds useful as starting material according to the present invention may e.g. be produced as follows:

EXAMPLE A 1-(1-Methylhydrazino)iminomethyl)piperazine a) S-Methyl-2-methyl-isothiosemicarbazide A solution of 239.8 g of S-methyl-2-methylisothio-semicarbazide in the form of a hydriodide in 100 ml of water is placed on a column filled with 1500 ml of a strong basic ion exchanger in chloride form (Amberlite IRA 420$^R$), and eluted with water. The fractions containing S-methyl-2-methylisothio-semi-carbazide in the form of a hydrochloride (HPLC) are lyophilised. The lyophilisate is treated with ether, isolated by filtration and dried.

S-methyl-2-methyl-isothiosemicarbazide in the form of a hydrochloride is obtained in the form of a white solid.

M.p.: 116° (isopropanol).

b) Benzylidene Derivative of 4-formyl-1-((1-methylhydrazino)imino-methyl)piperazine A solution of 40.9 g of S-methyl-2-methyl-isothiosemicarbazide in the form of a hydrochloride in 350 ml of ethanol is mixed with 30 g of freshly distilled formylpiperazine and heated under reflux for ca. 39 hours. The reaction mixture is cooled to room temperature, mixed with 26.4 ml of benzaldehyde and stirred for ca. 24 hours. The precipitate obtained is filtrated off, washed with ethanol and dried. The benzylidene derivative of 4-formyl-1-((1-methyl-hydrazino)imino-methyl)piperazine in the form of a hydrochloride is obtained.

c) 1-((1-Methylhydrazino)iminomethyl)piperazine

From 10 g of the benzylidene derivative of 4-formyl-1-((1-methylhydrazino) iminomethyl)-piperazine in the form of a hydrochloride the benaldehyde is split off by steam distillation under addition of 48 ml of 2N HCl. The aqueous slurry obtained is concentrated and an oily residue is obtained which is treated with boiling ethanol. The ethanolic phase is concentrated in vacuum. 1-((1-Methylhydrazino) iminomethyl)piperazine in the form of a dihydrochloride is obtained in the form of a white solid.

EXAMPLE B

1-[(1-Ethylhydrazino)iminomethyl]piperazine a) Benzylidene Derivative of 1-(hydrazinoiminomethyl) piperazine The pH of a solution of 10.7 g of the benzylidene derivative of 1-(hydrazinoiminomethyl)-piperazine in the form of a dihydrochloride in 100 ml of water is adjusted to 10 by addition of 8N NaOH. The mixture obtained is extracted with ethyl acetate. The ethyl acetate phase is dried and the solvent is evaporated off. The benzylidene derivative of 1-(hydrazinoimino-methyl)piperazine is obtained in the form of an amorphous powder.

b) Benzylidene Derivative of 1-formyl-4-(hydrazinoiminomethyl)piperazine 12.7 ml of acetic acid anhydride are added dropwise to 42 ml of ice-cooled formic acid, the mixture is stirred for ca. 1 hour and 16 g of the benzylidene derivative of 1-(hydrazinoimino-methyl) piperazine in 42 ml of formic acid are added dropwise. The mixture is left for ca. 2 hours at 0° and the solvent is evaporated off. The residue is treated with water and the pH of the mixture obtained is adjusted to pH 11 by addition of 10N KOH. The mixture is extracted with dichloromethane, the dichloromethane phase is dried and the solvent is evaporated off. The benzylidene derivative of 1-formyl4-(hydrazinoiminomethyl)piperazine is obtained in the form of a white powder.

c) Benzylidene Derivative of 1-[(1-ethylhydrazino)iminomethyl]-4-formylpiperazine An ice-cooled solution of 2 g of the benzylidene derivative of 1-formyl4-(hydrazino-iminomethyl) piperazine in 40 ml of dry tetrahydrofurane is treated with 9.3 ml of bis-(trimethyl-silyl)-lithiumamid (1M solution in tetrahydrofurane) and stirred for ca. 1 hour at 0°. 2.4 g of ethyl iodide are added to the reaction mixture and the mixture is stirred overnight at room temperature. The solvent is evaporated off and the residue is purified via "Dry-column-flash-chromatography": Eluent: 1. methanol; 2.90% methanol/10% acetic acid. Fractions containing the benzylidene derivative of 1-[(1-ethylhydrazino)iminomethyl]-4-formylpiperazine (analytical HPLC determination) are combined, the solvent is evaporated off and the benzylidene derivative of 1-[(1-ethylhydrazino)iminomethyl]4-formylpiperazine is obtained in the form of a white powder.

d) 1-[(1-Ethylhydrazino)iminomethyl]piperazine 2.7 g of the benzylidene derivative of 1-[(1-ethylhydrazino)iminomethyl]4-formylpiperazine dissolved in 11.6 ml of 2N HCl are treated by steam distillation. After evaporation of the water from the mixture obtained and drying of the residue 1-[(1-ethylhydrazino)iminomethyl] piperazine in the form of a dihydrochloride is obtained in the form of a white solid.

In the manner as described in Example B, but using the corresponding reactants the following compounds may be obtained:

EXAMPLE C

1-[(1-Allylhydrazino)iminomethyl]piperazine (in the form of a dihydrochloride)

EXAMPLE D

1-[[1-(4-Methoxybenzyl)hydrazino]iminomethyl] piperazine (in the form of a dihydrochloride)

EXAMPLE E

1-[[1-(3,4,5-Trimethoxybenzyl)hydrazino]iminomethyl] piperazine (in the form of a dihydrochloride)

EXAMPLE F

1-[(1-Methylhydrazino)(methylimino)methyl] piperazine a) Benzylidene Derivative of 1-formyl4-[hydrazino (methylimino)methyl]piperazine 37 g of 1-formyl4-[hydrazino(methylimino)methyl] piperazine in the form of a hydrochloride dissolved in a mixture of 80 ml of acetonitrile and 185 ml of water are treated with 30 g of benzaldehyde. The mixture is stirred for ca. 3 hours at room temperature and extracted with ether. The water of the aqueous phase is evaporated. The residue is treated with water and a pH of 11 of the mixture is adjusted with 2N NaOH. The mixture is extracted with dichloromethane, the organic phase is dried, the solvent evaporated and the residue is dried. The benzylidene derivative of 1-formyl4-[hydrazino(methylimino)methyl] piperazine is obtained in the form of a white powder.

b) Benzylidene Derivative of 1-formyl-4-[(1-methylhydrazino)methylimino)methyl]piperazine A solution of 1,62 g of the benzylidene derivative of 1-formyl-4-[hydrazino(methylimino)-methyl]piperazine in 30 ml of acetonitrile is treated with 4,56 g of methyl iodide and the mixture is refluxed overnight. The solvent is evaporated off and the residue is stirred with 20 ml of water and 10 ml Amberlite IRA-400 (Cl)$^R$ (ion exchange resin) for ca. 1 hour at room temperature. The mixture is filtrated. The aqueous solution is adjusted to a pH of 11 with 2N NaOH and extracted with dichloromethane. The organic phase is dried and concentrated by solvent evaporation. For purification the concentrate is treated in the manner as described in Example B, c).The benzylidene derivative of 1-formyl4-[(1-methylhydrazino) (methylimino)-methyl]piperazine is obtained in the form of a white powder.

c) 1[[(1-Methylhydrazino)(methylimino)methyl]piperazine 1.14 g of the benzylidene derivative of 1-formyl4-[(1-methylhydrazino)(methylimino) methyl]-piperazine dissolved in 6 ml of 2N HCl are treated in the manner as described in Example Bd). 1-[(1-Methylhydrazino) (methylmino)methyl]piperazine in the form of a dihydrochloride is obtained in the form of a white solid.

EXAMPLE G

In the manner as described in Example F but using the corresponding reactants 1-[(1-methylhydrazino) (ethylimino)methyl]piperazine (in the form of a dihydrochloride) is obtained.

EXAMPLE H

Glycine-(4-hydrazinoimometlyl)piperazide a) Benzylidene Derivative of 1-(hydrazinoiminomethyl) piperazine 15 g of 1-(hydrazinoiminomethyl)piperazine in the form of a dihydrochloride in a mixture of 50 ml of methanol and 50 ml of water are treated with 12 g of benzaldehyde. The mixture is stirred for ca. 1 hour at room temperature and extracted with ether. The aqueous phase is evaporated off and the residue is treated with absolute methanol. The solvent is evaporated off and the benzylidene derivative of 1-(hydrazinoiminomethyl)piperazine in the form of a dihydrochloride is obtained in form of a colourless powder.

b) Benzylidene Derivative of N-benzyloxycarbonylglycin-(4-hydrazinoiminomethyl)piperazide 2 g of benzyloxycarbonyl-glycine-N-succinimidylester in 50 ml of absolute methylenchloride are treated with 2 g of triethylamine and with 2 g of the benzylidene derivative of 1-(hydrazinoiminomethyl)piperazine in the form of a dihydrochloride. The mixture is stirred for ca. 20 minutes at room temperature. The benzylidene derivative of N-benzyloxycarbonylglycin-(4-hydrazinoiminomethyl) piperazide precipitates, is filtrated off and dried.

c) Glycine-(4-hydrazinoiminomethyl)piperazide

A mixture of 2.3 g of N-benzyloxycarbonylglycin-(4-hydrazinoiminomethyl)piperazide, 60 ml of ethanol, 5.5 ml of 2 N HCl and 1.2 g of 10% palladium on charcoal are treated with hydrogen in an autoclave under stirring at room temperature. After ca. 12 hours the mixture is filtrated and the solvent in the filtrate is evaporated off. The residue is treated with ethanol and ethanol is evaporated off. Glycine-(4-hydrazinoiminomethyl)piperazide in the form of a dihydrochloride is obtained in form of a white powder.

EXAMPLE I 1,4-bis-(Hydrazinoiminomethyl)piperazine a) 1.4-bis-Thiocarbamoylpiperazine 4.4 g of 1,4-dicyanopiperazine in a solution of 3.5 g hydrogen sulfide and 1.5 g of triethylamine in 150 ml of ethanol are heated in an autoclave at 110° for ca. 3 hours and the mixture is cooled to room temperature. 1,4-bis-thiocarbamoylpiperazine in the form of a dihydrochloride precipitates, is filtrated off and dried.

b) 1,4-Bis-[imino(methylthiomethyl]piperazine 5.5 g of 1,4-bis-thiocarbamoylpiperazine in 150 ml of methanol ar treated with 15 g of methyliodide. The mixture obtained is heated under reflux for ca. 5 hours and stirred for ca. 43 hours at room temperature. A precipitate of 1,4-bis-[imino(methylthio)-methyl]-piperazine in the form of a dihydroiodide is obtained, filtrated off, washed with methanol, dried, dissolved in water and treated with a strong basic ion exchange resin in the chloride form under stirring for ca. 24 hours. The ion exchange resin is filtrated off and the filtrate is lyophilised. 1,4-bis-[imino(methyl-thio) methyl]piperazine in the form of a dihydrochloride is obtained.

c) 1,4-Bis-(hydrazinoiminomethyl)piperazine 4.2 g of 1,4-bis-[imino(methyl-thio)methyl]piperazine in the form of a dihydrochloride in 60 ml of water are treated with 1.45 g of hydrazine hydrate. The mixture is stirred for ca.15 hours at room temperature and the solvent is evaporated off. The residue is dissolved in 15 ml of hot water. 400 ml of ethanol are added to the solution obtained and the mixture is stirred at room temperature and at 0°. 1,4-Bis-(hydrazinoiminomethyl)piperazine in the form of a dihydrochloride precipitates, is filtrated off and dried.

EXAMPLE J 1-(Hydrazinoiminomethyl)4-[(ethylimino)[(3-dimethylaminopropyl)amino]methyl]piperazine a) Benzylidene Derivative of 1-(hydrazinoiminomethyl) piperazine The pH of a m mixture of 10.7 g of the benzylidene derivative of 1-(hydrazinoiminomethyl)-piperazine in the form of a dihydrochloride (obtained according to Example H, a)) in 100 ml of water is adjusted to 10 with 8 N NaOH. The mixture is extracted with ethyl acetate. The ethyl acetate phase is dried over $Na_2SO_4$ and the solvent is evaporated off. The benzylidene derivative of 1-(hydrazinoiminomethyl) piperazine is obtained in form of a powder.

b) Benzylidene Derivative of 1-(hydrazinoiminomethyl)-4-[(ethyl-imino)[(3-dimethyl-aminopropyl)amino]methyl] piperazine 1 g of 1-(hydrazinoiminomethyl)piperazine in 5 ml of dimethylformamide are treated with 828 mg of 1-(3-dimethylaminopropyl)-3-ethylcarbodiimid in the form of a hydrochloride and stirred for ca. 1 week at room temperature. The mixture is introduced into 100 ml of ether. An oil precipitates. The oil obtained is dissolved in acetonitrile and the solution obtained is treated with 8.6 ml of 1N etheric hydrochloric acid. The benzylidene derivative of 1-(hydrazinoiminomethyl)-4-[(ethyl-imino)[(3-dimethylaminopropyl)amino]methyl]piperazine in the form of a trihydrochloride crystallizes, is filtrated off and dried.

c) 1-(Hydrazinoiminomethyl)-4-[(ethylimino)[(3-dimethylaminopropyl) amino]methyl]-piperazine 1.4 g of the benzylidene derivative of 1-(hydrazinoiminomethyl)-4-[(ethyl-imino)[(3-dimethylaminopropyl)amino]methyl]piperazine in the form of a trihydrochloride are heated in 20 ml of water and distilled under addition of water until no further benzaldehyde is distilled off. The water in the destination residue is evaporated off and the residue is treated with isopropanol and the isopropanol is distilled off (3 times). 1-(Hydrazinoiminomethyl)-4-[(ethylimino)[(3-dimethylaminopropyl)amino]methyl]piperazins in the form of a trihydrochloride is obtained in the form of a white solid.

EXAMPLE L

[6(R)-6α,7β(Z)]-7-[[(5-Amino-1,2,4-thiadiazol-3-yl)-(fluormethoxyimino)acetyl]amino]-3-formyl-3-cephem-4-carboxylic acid-1-(isopropoxycarbonyloxy)ethylester a) [6(R)-6α,7β(Z)]-7-[[(5-Amino-1,2,4-thiadiazol-3-yl)-(fluormethoxy-imino-)acetyl]amino-]-3-formyl-3-cephem-4-carboxylic Acid 0.4 ml of Hünig-base are added dropwise to 1 g of N-(1,4,5a,6-Tetrahydro-3-hydroxy-1,7-dioxo-3H,7H-azeto[2,1-b]furo[3,4-d][1,3]thiazin-6-yl)-2-(5-amino-1,2,4-thiadiazol-3-yl)-(Z)-2-(fluormethoxyimino)acetic acid amide in 76 ml of acetonitrile. The solution obtained is treated with 0.38 g of sodium iodide dissoluted in 5 ml of acetonitrile. [6(R)-6α,7β(Z)]-7-[[(5-Amino-1,2,4-thiadiazol-3-yl)-(fluormethoxy-amino)acetyl]amino]-3-formyl-3-cephem4-carboxylic acid in the form of a sodium salt precipitates, is filtrated off and dried.

b) [6(R)-6α,7β(Z))-7-[[(5-Amino-1,2,4-thiadiazol-3-yl)-fluormethoxyimino) acetyl]amino]-3-formyl-3-cephem-4-carboxylic acid-1-(isopropoxycarbonyloxy)ethylester 1 g of [6(R)-6α,7β(Z)]-7-[[(5-Amino-1,2,4-thiadiazol-3-yl)-(fluormethoxy-imino) acetyl]-amino]-3-formyl-3-cephem-4-carboxylic acid in the form of a sodium salt in 10 ml of dimethyl-acetamide is treated at 0° under stirring with a solution of 0,65 g of 1-iodoethylisopropylcar-bonate in 4 ml of toluene and the mixture obtained is stirred for ca. 90 minutes at 0°. The mixture obtained is diluted with 100 ml of ethyl acetate and extracted with an aqueous potassium hydrogencarbonate solution. The organic phase is extracted with water, dried over $NA_2SO_4$ and concentrated to a volume of 10 ml. The concentrate obtained is introduced into 120 ml of n-hexane. A mixture of two diastereoisomers in a ratio of ca. 1:1 of [6(R)-6α7β(Z))-7-[[(5-Amino-1,2,4-thiadiazol-3-yl)-fluormethoxyimino)-acetyl]amino]-3-formyl-3-cephem-4-carboxyylic acid-1-(isopropoxycarbonyloxy)ethylester precipitates, is filtrated off, dried and obtained in form of a solid.

EXAMPLE K 1-(R)-(Amino(4-hydroxyphenyl)acetyl)4-(hydrazinoiminomethyl)piperazine a) Benzylidene Derivative of 1-(R)-(amino(4-hydroxyphenyl)acetyl)4-(hydrazinoimino-methyl) piperazine 4.85 g (R)-4-Hydroxy-α-[(3-methoxy-1-methyl-3-oxo-1-propenyl)amino]-phenylacetic acid in the form of a potassium salt in 30 ml methylene chloride are treated under stirring with 1.28 g of dimethylacetamide and 1 drop of 3-picoline. The mixture obtained is cooled to ca. −30°, treated with 2 g of pivaloylchloride in 10 ml of methylene chloride and stirred for ca. 35 minutes at ca. −12°. The mixture obtained is cooled to −40° and treated with a mixture which is cooled to 0° of 5 g of the benzylidene derivative of 1-(hydrazinoiminomethyl)piperazine in the form of a dihydrochloride and 3.4 g of triethylamine in 30 ml of methylene chloride. The mixture obtained is stirred for ca. 20 minutes at ca. −30° and for ca. 20 minutes at −10°, treated at 0° with a mixture of 75 ml of water, 10 ml conc. HCl and 6 ml of methylene chloride, stirred for ca. 20 minutes at 0° and warmed to room temperature. A two-phase mixture is obtained. The phases are separated and the pH of the aqueous phase is adjusted to 8.0 with triethylamine. The benzylidene derivative of 1-(R)-(amino(4-hydroxyphenyl)acetyl)4-(hydrazinoimino-methyl)piperazine precipitates, is filtrated off, dried and obtained in the form of a white solid.

b) 1-(R)-(Amino(4-hydroxyphenyl)acetyl)4-(hydrazinoimino-ethyl)piperazine

A mixture of 0.3 g of the benzylidene derivative of 1-(R)-(amino(4-hydroxyphenyl)acetyl)4-(hydrazino-imino-methyl)piperazine, 60 ml of ethanol, 1 ml of 2N HCl and 0.1 g of 10% palladium on charcoal are treated with hydrogen in an autoclave under stirring overnight at room temperature. The mixture obtained is filtrated and the filtrate is concentrated in vacuo. The concentrate obtained is treated with 50 ml of ethanol and the solvent is evaporated off. 1-(R)-(Amino(4-hydroxyphenyl)acetyl)4-(hydrazinoiminoethyl)-piperazine in the form of a trihydrochloride is obtained in the form of a white solid.

$^1$H-NMR-Spectra

Ex.

1: 3,25 (broad, 4H, —CH$_2$—N—CH$_2$—); 3,3 (s, 3H, N—CH$_3$); 3,60 and 4,28 (AB quartet, J=18 Hz, 2H, SCH$_2$); 3,74 (broad, 4H, —CH$_2$—NH$^+$—CH$_2$—); 5,28 (d, J=5 Hz, 1H, β-lactanm-H); 5,78 (d, J=55 Hz, 2H, CH$_2$F); 5,91 (dd, J=5 and 8,3 Hz, 1H, β-lactam-H); 8,1 (s, 1H, CH=N); 9,04 (broad singulet, 1H, NH); 9,35 (broad singulet, 1H, NH); (9,81 (d, J=8,3 Hz, 1H, NH), 9,9 (broad singulet, 2H, NH$_2$).

2: 1.17, t, J=5 Hz, 3H, CH$_3$; 3.28, b, 4H, N—CH$_2$; 3.60 and 4.21, AB-quartet, J=18 Hz, 2H, S—CH$_2$; 3.67, b, 4H, N—CH$_2$, 3.91, m, 2H, CH$_2$; 5.22, d, J=5 Hz, 1H, β-lactam-H, 5.82, d, J=55 Hz, 2H, CH$_2$F; 5.85, dd, J=5 Hz and 8 Hz, 1H, β-lactam-H; 8.35, b, 3H, 1H CH=N and 2H, NH; 9.78, d, J=8 Hz, 1H, NH.

3: 1.18, t, J=5 Hz, 3H, CH$_3$; 3.30, b, 9H, 4H of NCH$_2$ and 2H of CH$_2$ and 3H of CH$_3$; 3.70, m, 5H, 4H of NCH$_2$ and 1H of S—CH$_2$; 4.10, part of AB-quartet, J=18 Hz, 1H, SCH$_2$; 5.32, d, J=5 Hz, 1H, β-lactam-H; 5.82, d, J=55 Hz, 2H, CH$_2$F; 5.95, dd, J=5 Hz and 8 Hz, 1H, β-lactam-H; 8.08, s, 1H, CH=N; 8.32, b, 1H, NH; 9.82, d, J=8 Hz, 1H, NH.

4: 3.30, b, 4H, N—CH$_2$; 3.58 and 4.25, AB-quartet, J=18 Hz, 2H, S—CH$_2$; 3.73, b, 4H, N—CH$_2$; 4.30, m, 2H, N—CH$_2$; 5.26, m, 3H, 1H β-lactam-H and 2H of CH$_2$=C; 5.64, part of dublet, 1H, CH$_2$F; 5.90, m, 4H, 1H of CH$_2$—F and 1H of CH=C adn 1H β-lactam-H; 8.11, s, 1H, CH=N; 9.81, d, J=8 Hz, 1H, NH.

5: 90 and 03, 2s (2:1), 3H, N-3-CH$_3$; 3.33, b, 7H, 4H of —CH$_2$ and H$_3$3.64, b, 5H, 4H of NH$_2$ and 1H of S—CH$_2$; 4.15, part of AB-quartet; J=18 Hz, 1H, S—CH$_2$; 5.21, d, J=5 Hz, 1H, β-lactam-H; 5.81, d, J=55 Hz, 2H, CH$_2$F; 5.83, dd, J=5 Hz and J=8 Hz, 1H, β-lactam-H; 8.32, 3H, 1H of CH=N and 2H of NH; 9.79, d, J=8 Hz, 1H, NH.

6: 3.31, b, 4H, N—CH$_2$; 3.52 and 4.18, AB-quartet, J=18 Hz, 2H, S—CH$_2$, 3.72, b, 7H, 4H of N—CH$_2$ and 3H of OCH$_3$; 4.95, AB-quartet, J=17 Hz, 2H, CH$_2$; 5.14, d, J=5 Hz, 1H, β-lactam-H; 5.78, d, J=55 Hz, 2H, CH$_2$F; 5.77, dd, J=5 Hz and 8 Hz, 1H, β-lactam-H; 6.86–6.91, m, 2H, CH— arom.; 7.15–7.19, m, 2H, CH-arom.; 8.26, b, 2H, CH=N and NH; 8.40, b, 1H, NH; 9.74, d, J=8 Hz; 1H, NH.

7: 3.34, b, 4H, N—CH$_2$; 3.57 and 4.23, AB-quartet, J=18 Hz, 2H, S—CH$_2$; 3.64, s, 3H, OCH$_3$; 3.79, b, 10H, 4H of N—CH$_2$ and 6H of OCH$_3$; 5.03, AB-quartet, J=17 Hz, 2H, CH$_2$; 5.27, d, J=5 Hz, 1H, β-lactam-H; 5.81, d, J=55 Hz, 2H, CH$_2$F; 5.92, dd, J=5 Hz and 8 Hz, 1H, β-lactam-H; 6.53, s, 2H, CH-arom.; 8.14, s, 1H, CH=N; 8.30, b, 2H, NH; 9.83, d, J=8 Hz, 1H, NH.

8: 1.20, t, J=7.1 Hz, 3H, CH$_3$; 3.5, b, 4H, N—CH$_2$; 3.55 and 4.51, AB-quartet, J=18.2 Hz, 2H, S—CH$_2$; 3.6, b, 4H, N—CH$_2$; 4.07, q, J=7.1 Hz, 2H, O—CH$_2$; 5.30, d, J=5.0 Hz, 1H, β-lactam-H; 5.88, dd, J=5.0 Hz and J=7.9 Hz, 1H, b-lactam-H; 6.84, s, 1H, CH thiazol; 8.4, b, 2H, NH; 8.66, s, 1H, CH=N; 9.72, d, J=7.9 Hz, 1H, NH; 12.3, b, 1H, OH; 12.4, b, 1H, OH.

9: 3.4–3.8, m,b, 8H, N—CH$_2$; 3.56 and 4.53, AB-quartet, J=18 Hz, 2H, S—CH$_2$; 3.8–4.0, m, 2H, N—CH$_2$; 5.30, d, J=5.0 Hz, 1H, β-lactam-H; 5.88, dd, J=5.0 Hz and J=7.9 Hz, 1H, β-lactam-H; 6.84, s, 1H, CH thiazol; 8.2–8.5, b, 4H, NH; 8.69, s, 1H, CH=N; 9.72, d, J=7.9 Hz, 1H, NH; 10.1–10.3, b, 1H, NH; 12.4, b, 2H, OH.

10: 3.56 and 4.52, AB-quartet, J=18.0 Hz, 2H, S—CH$_2$; 3.7, b, 8H, N—CH$_2$; 5.30, d, J=5.0 Hz, 1H, β-lactam-H; 5.89, dd, J=5.0 Hz and J=7.8 Hz, 1H, β-lactam-H; 6.85, s, 1H, CH thiazol; 7.4–7.5, m, 5H, CH arom.; 8.4, b, 2H, NH; 8.67, s, 1H, CH=N; 9.74, d, J=7.8 Hz, 1H, NH; 12.3, b, 1H, OH; 12.4, b, 1H, OH.

11: 2.04, s, 3H, CH$_3$; 3.55 and 4.53, AB-quartet, J=18.0 Hz, 2H, S—CH$_2$; 3.6, b, 8H, N—H$_2$; 5.31, d, J=5.0 Hz, 1H, β-lactam-H; 5.90, dd, J=5.0 Hz and J=7.9 Hz, 1H, β-lactam-H; 6.84, s, 1H, CH thiazol; 8.3, b, 2H, NH; 8.62, s, 1H, CH=N; 9.79, d, J=7.9 Hz, 1H, NH, 12.1, b, 1H, OH; 12.4, b, 1H, OH.

12: 3.55 and 4.53, AB-quartet, J=18.0 Hz, 2H, S—CH$_2$; 3.6, b, 8H, N—CH$_2$; 3.77, s, 2H, C—CH$_2$; 5.30, d, J=5.0 Hz, 1H, β-lactam-H; 5.89, dd, J=5.0 Hz and J=7.9 Hz, 1H, β-lactam-H; 6.84, s, 1H, CH thiazol; 7.2–7.4, m, 5H, CH arom.; 8.3, b, 2H, NH; 8.64, s, 1H, CH=N; 9.78, d, J=7.9 Hz, 1H, NH; 12.2, b, 1H, OH; 12.5, b, 1H, OH.

13: 3.3–3.5, m, 2H, N—CH$_2$; 3.56 and 4.50, AB-quartet, J=18.0 Hz, 2H, S—CH$_2$; 3.6–3.8, m,b, 6H, N—CH$_2$; 5.30, d, J=5.0 Hz, 1H, β-lactam-H; 5.89, dd, J=5.0 Hz and J=7.9 Hz, 1H, β-lactam-H; 6.84, s, 1H, CH thiazol; 6.97, s, 1H, CH thiazol; 8.4, b, 2H, NH; 8.64, s, 1H, CH=N; 9.71, d, J=7.9 Hz, 1H, NH; 12.2, b, 2H, OH; 12.3, b, 1H, OH.

14: 2.77, s, 6H, N—CH$_3$; 3.1–3.3, m, 4H, N—CH$_2$; 3.56 and 4.51, AB-quartet, J=18.0 Hz, 2H, S—CH$_2$; 3.5–3.7, m, 4H, N—CH$_2$; 5.30, d, J=5.0 Hz, 1H, β-lactam-H; 5.89, dd, J=5.0 Hz and J=7.8 Hz, 1H, β-lactam-H; 6.85, s, 1H, CH thiazol; 8.3, b, 2H, NH; 8.65, s, 1H, CH=N; 9.74, d, J=7.8 Hz, 1H, NH; 12.2, b, 1H, OH; 12.4, b, 1H, OH.

15: 3.5–3.8, m,b, 8H, N—CH$_2$; 3.56 and 4.52, AB-quartet, J=18 Hz, 2H, S—CH$_2$; 4.87, s, 2H, O—CH$_2$; 5.31, d, J=4.9 Hz, 1H, β-lactam-H; 5.89, dd, J=5.0 Hz and J=7.8 Hz, 1H, β-lactam-H; 6.83, s, 1H, CH thiazol; 6.9–7.0, m, 3H, CH arom.; 7.2–7.4, m, 2H, CH arom.; 8.3, b, 2H, NH; 8.65, s, 1H, CH=N; 9.70, d, J=7.8 Hz, 1H, NH; 12.2, b, 1H, OH; 12.3, b, 1H, OH.

16: 1.7–2.0, m, 3H, C—CH$_2$; 2.3–2.5, m, 1H, C—CH$_2$; 3.1–3.3, m, 2H, N—CH$_2$; 3.3–3.9, m,b, 8H, N—CH$_2$; 3.56 and 4.50, AB-quartet, J=18.1 Hz, 2H, S—CH$_2$; 4.6–4.8, m, 1H, N—CH; 5.30, d, J=5.0 Hz, 1H, β-lactam-H; 5.90, dd, J=5.0 Hz and J=7.9 Hz, 1H, β-lactam-H; 6.79, s, 1H, CH thiazol; 8.3, b, 2H, NH; 8.5, b, 2H, NH; 8.63, s, 1H, CH=N; 9.63, d, J=7.9 Hz, 1H, NH; 10.1–10.3, b, 1H, NH; 12.0, b, 1H, OH; 12.2, b, 1H, OH.

17: 2.25, s, 3H, CH$_3$; 3.3, b, 2H, N—CH$_2$; 3.56 and 4.52, AB-quartet, J=18 Hz, 2H S—CH$_2$; 3.6, b, 2H, N—CH$_2$; 3.7, b, 4H, N—CH$_2$; 5.30, d, J=5.0 Hz, 1H, β-lactam-H;

5.89, dd, J=5.0 Hz and J=7.8 Hz, 1H, β-lactam-H; 6.85, s, 1H, CH thiazol; 7.2–7.4, m, 4H, CH arom.; 8.4, b, 2H, NH; 8.66, s, 1H, CH=N; 9.74, d, J=7.9 Hz, 1H, NH; 12.3, b, 1H, OH; 12.4, b, 1H, OH.

18: 3.2, b, 2H, N—CH$_2$; 3.53 and 4.58, AB-quartet, J=18.2 Hz, 2H, S—CH$_2$; 3.5, b, 4H, N—CH$_2$; 3.8, b, 2H, N—CH$_2$; 5.29, d, J=5.0 Hz, 1H, β-lactam-H; 5.7, m,b, 1H, N—CH; 5.88, dd, J=5.0 Hz and J=8.0 Hz, 1H, β-lactam-H; 6.81, s, 1H, CH thiazol; 7.4–7.6, m, 5H, CH arom.; 8.3, b, 2H, NH; 8.62, s, 1H, CH=N; 8.8, b, NH; 9.67, d, J=8.0 Hz, 1H, NH; 12.2, b, 2H, OH.

19: 3.0–3.3, m,b, 2H, N—CH$_2$; 3.5–3.8, m,b, 6H, N—CH$_2$; 3.53 and 4.47, AB-quartet, J=18.3 Hz, 2H, S—CH$_2$; 5.29, d, J=5.1 Hz, 1H, β-lactam-H; 5.5, m, 1H, N—CH; 5.88, dd, J=5.0 Hz and J=7.9 Hz, 1H, β-lactam-H; 6.81, s, 1H, CH thiazol; 6.8–6.9, m, 2H, CH arom.; 7.2–7.4, m, 2H, CH arom.; 8.3, b, 2H, NH; 8.5, b, 3H, NH; 8.60, s, 1H, CH=N; 9.67, d, J=7.9 Hz, 1H, NH; 12.2, b, 2H, OH.

20: 1.5–1.9, m, 4H, C—CH$_2$; 3.1–3.3, m,b, 2H, N—CH$_2$; 3.5–3.9, m,b, 8H, N—CH$_2$; 3.56 and 4.51, AB-quartet, J=18.1 Hz, 2H, S—CH$_2$; 4.48, 1H, N—CH; 5.30, d, J=5.1 Hz, 1H, β-lactam-H; 5.89, dd, J=5.0 Hz and J=7.9 Hz, 1H, β-lactam-H; 6.82, s, 1H, CH thiazol; 8.1, b, 2H, NH; 8.4, b, NH; 8.65, s, 1H, CH=N; 9.69, d, J=7.9 Hz, 1H, NH; 12.2, b, 2H, OH.

21: 3.4–3.7, m,b, 9H, N—CH$_2$/S—CH$_2$; 4.13, s, 2H, O—CH$_2$; 4.50, J=18.1 Hz, 1H, S—CH$_2$; 5.30 d, J=5.0 Hz, 1H, β-lactam-H; 5.89, dd, J=5.0 Hz and J=7.9 Hz, 1H, β-lactam-H; 6.81, s, 1H, CH thiazol; 8.3, b, 2H, NH; 8.62, s, 1H, CH=N; 9.67, d, J=7.9 Hz, 1H, NH; 12.1, b, 2H, OH.

22: 1.4–1.9, m, 4H, C—CH$_2$; 3.1–3.3, m,b, 2H, N—CH$_2$; 3.5–4.0, m,b, 8H, N—CH$_2$; 3.56 and 4.52, AB-quartet, J=18.0 Hz, 2H, S—CH$_2$; 4.49, b, 1H, N—CH; 5.30, d, J=5.1 Hz, 1H, β-lactam-H; 5.89, dd, J=5.1 Hz and J=7.9 Hz, 1H, β-lactam-H; 6.81, s, 1H, CH thiazol; 8.11, m, 1H, NH; 8.4, b, NH; 8.67, s, 1H, CH=N; 9.68, d, J=7.8 Hz, 1H, NH; 12.2, b, 1H, OH; 12.3, b, 1H, OH.

23: 1.8–2.1, m,b, 2H, C—CH$_2$; 2.3–2.6, m,b, 2H, C—CH$_2$; 3.4–3.9, m,b, 8H, N—CH$_2$; 3.55 and 4.52, AB-quartet, J=18 Hz, 2H, S—CH$_2$; 4.4, m,b, 1H, N—CH; 5.30, d, J=5.0 Hz, 1H, β-lactam-H; 5.88, dd, J=5.0 Hz and J=7.9 Hz, 1H, β-lactam-H; 6.81, s, 1H, CH thiazol; 8.4, b, NH; 8.67, s, 1H, CH=N; 9.69, d, J=8.0 Hz, 1H, NH; 12.2, b, 1H, OH; 12.3, b, H, OH.

24: 0.87, t, J=7.3 Hz, 3H, CH$_3$; 0.94, d, J=6.7 Hz, 3H, CH$_3$; 1.0–1.3, m, 1H, C—CH$_2$, C—CH; 1.4–1.6, m, 1H, C—CH$_2$, C—CH; 1.7–1.9, m, 1H, C—CH$_2$, C—CH; 3.4–4.0, m,b, 8H, N—CH$_2$; 3.55 and 4.51, AB-quartet, J=18.0 Hz, 2H, S—CH$_2$; 4.31, m, 1H, N—CH; 5.30, d, J=5.0 Hz, 1H, β-lactam-H; 5.89, dd, J=5.0 Hz and J=7.9 Hz, 1H, β-lactam-H; 6.81, s, 1H, CH thiazol; 8.3, b, NH; 8.67, s, 1H, CH=N; 9.68, d, J=7.9 Hz, 1H, NH; 12.2, b, 1H, OH; 12.4, b, 1H, OH.

25: 0.85, b, 3H, CH$_3$; 1.2, b, 6H, C—CH$_2$; 1.5, b, 2H, C—CH$_2$; 2.33, t,b, 7 H, 2H, C—CH$_2$; 3.3–3.8, m,b, 9H, N—CH$_2$, S—CH$_2$; 4.54, J=18.1 Hz, 1H, S—CH$_2$; 5.30, d, J=4.9 Hz, 1H, βlactam-H; 5.89, dd, J=5 Hz and J=8 Hz, 1H, β-lactam-H; 6.85, s, 1H, CH thiazol; 8.4, b, NH; 8.66, s, 1H, CH=N; 9.79, d, J=7.8 Hz, 1H, NH; 12.3, b, 1H, OH; 12.5, b, 1H, OH.

26: 0.84, t,b, J=6.5 Hz, 3H, CH$_3$; 1.2, b, 28H, C—CH$_2$; 1.47, m,b, 2H, C—CH$_2$; 2.33, t, J=7 Hz, 2H, C—CH$_2$; 3.4–3.8, m,b, 9H, N—CH$_2$, S—CH$_2$; 4.53, J=18.0 Hz, 1H, S—CH$_2$; 5.31, d, J=4.9 Hz, 1H, β-lactam-H; 5.90, dd, J=5 Hz and J=8 Hz, 1H, β-lactam-H; 6.85, s, 1H, CH thiazol; 8.4, b, 2H, NH; 8.65, s, 1H, CH=N; 9.78, d, J=7.9 Hz, 1H, NH; 12.2, b, 1H, OH; 12.4, b, 1H, OH.

27: 0.85, t, J=6 Hz, 3H, CH$_3$; 1.24, 24H, C—CH$_2$; 1.5, m,b, 2H, C—CH$_2$; 2.33, t, J=7 Hz, 2H, C—CH$_2$; 3.4–3.7, m,b, 9H, N—CH$_2$, S—CH$_2$; 4.52, J=18.0 Hz, 1H, S—CH$_2$; 5.31, d, J=5.0 Hz, 1H, β-lactam-H; 5.90, dd, J=5 Hz and J=8 Hz, 1H, β-lactam-H; 6.83, s, 1H, CH thiazol; 8.3, b, 2H, NH; 8.61, s, 1H, CH=N; 9.74, d, J=7.9 Hz, 1H, NH; 12.1, b, 1H, OH; 12.3, b, 1H, OH.

28: 0.86, t, J=6.5 Hz, 3H, CH$_3$; 1.26, 8H, C—CH$_2$; 1.49, m,b, 2H, C—CH$_2$; 2.33, t, J=7 Hz, 2H, C—CH$_2$; 3.4–3.8, m,b, 9H, N—CH$_2$, S—CH$_2$; 4.52, J=18.1 Hz, 1H, S—CH$_2$; 5.30, d, J=5.0 Hz, 1H, β-lactam-H; 5.89, dd, J=5.0 Hz and J=7.8 Hz, 1H, β-lactam-H; 6.79, s, 1H, CH thiazol; 8.3, b, 2H, NH; 8.62, s, 1H, CH=N; 9.69, d, J=7.8 Hz, 1H, NH; 12.1, b, 2H, OH.

29: 3.3–3.9, m,b, 11H, N—CH$_2$, S—CH$_2$, O—CH$_2$; 4.37, t, J=5.5 Hz, 1H, O—CH; 4.50, J=18.9 Hz, 1H, S—CH$_2$; 5.30, d, J=5.0 Hz, 1H, β-lactam-H; 5.90, dd, J=5.0 Hz and J=7.9 Hz, 1H, β-lactam-H; 6.83, s, 1H, CH thiazol; 8.3, b, 2H, NH; 8.62, s, 1H, CH=N; 9.70, d, J=7.9 Hz, 1H, NH; 12.1, b, 1H, OH; 12.3, b, 1H, OH.

30: 3.5–3.8, m,b, 8H, N—CH$_2$; 3.51 and 4.54, AB-quartet, J=18.1 Hz, 2H, S—CH$_2$; 4.87, s, 2H, O—CH$_2$; 5.29, d, J=5.1 Hz, 1H, β-lactam-H; 5.79, d, J=55.6 Hz, 2H, F—CH$_2$; 5.92, dd, J=5.0 Hz and J=8.1 Hz, 1H, β-lactam-H; 6.9–7.0, m, 3H, CH arom.; 7.2–7.4, m, 2H, CH arom.; 8.3, b, NH; 8.64, s, 1H, CH=N; 9.81, d, J=8.2 Hz, 1H, NH; 12.2, b, 1H, OH.

31: 2.25, s, 3H, CH$_3$; 3.2–3.9, m,b, 8H, N—CH$_2$; 3.51 and 4.52, AB-quartet, J=18.2 Hz, 2H, S—CH$_2$; 5.29, d, J=5.0 Hz, 1H, β-lactam-H; 5.79, d, J=55.0 Hz, 2H, F—CH$_2$; 5.92, dd, J=5 Hz and J=8 Hz, 1H, β-lactam-H; 7.2–7.6, m, 4H, CH arom.; 8.1–8.5, b, 4H, NH; 8.61, s, 1H, CH=N; 9.80, d, J=8.3 Hz, 1H, NH; 12.2, b, 1H, OH.

32: 2.04, s, 3H, CH$_3$; 3.3–3.8, m,b, 9H, N—CH$_2$, S—CH$_2$; 4.55, J=18.2 Hz, 1H, S—CH$_2$; 5.29, d, J=5.0 Hz, 1H, β-lactam-H; 5.79, d, J=56.0 Hz, 2H, F—CH$_2$; 5.93, dd, J=5 Hz and J=8 Hz, 1H, β-lactam-H; 8.3, b, NH; 8.62, s, 1H, CH=N; 9.84, d, J=8.2 Hz, 1H, NH; 12.2, b, 1H, OH.

33: 1.7–2.0, m, 3H, C—CH$_2$; 2.2–2.5, m, 1H, C—CH$_2$; 3.1–3.4, m, 2H, N—CH$_2$; 3.3–3.9, m,b, 8H, N—CH$_2$; 3.50 and 4.54, AB-quartet, J=18.2 Hz, 2H, S—CH$_2$; 4.6–4.8, m, 1H, N—CH; and J=8.2 Hz, 1H, β-lactam-H; 8.5, b, NH; 8.68, s, 1H, CH=N; 9.81, d, J=7.9 Hz, 1H, NH; 10.4, b, 1H, NH; 12.5, b, 1H, OH.

34: 3.4–3.8, m,b, 8H, N—CH$_2$; 3.50 and 4.55, AB-quartet, J=18.2 Hz, 2H, S—CH$_2$; 3.9, m, 2H, N—CH$_2$; 5.28, d, J=5.0 Hz, 1H, β-lactam-H; 5.78, d, J=56.7 Hz, 2H, F—CH$_2$; 5.91, dd, J=5.0 Hz and J=8.3 Hz, 1H, β-lactam-H; 8.3, b, NH; 8.68, s, 1H, CH=N; 9.81, d, J=8.3 Hz, 1H, NH; 12.4, b, 1H, OH.

35: 0.85, t, J=7.2 Hz, 3H, CH$_3$; 0.92, d, J=6.8 Hz, 3H, CH$_3$; 1.0–1.3, m, 1H, C—CH$_2$, C—CH; 1.4–1.6, m, 1H, C—CH$_2$, C—CH; 1.7–1.9, m, 1H, C—CH$_2$, C—CH; 3.3–4.0, m,b, 8H, N—CH$_2$; 3.50 and 4.54, AB-quartet, J=18.2 Hz, 2H, S—CH$_2$; 4.30, m,b, 1H, N—CH; 5.28, d, J=5.0 Hz, 1H, β-lactam-H; 5.78, d, J=58.1 Hz, 2H, F—CH$_2$; 5.90, dd, J=5.0 Hz and J=8.2 Hz, 1H, β-lactam-H; 8.4, b, NH; 8.68, s, 1H, CH=N; 9.81, d, J=7.9 Hz, 1H, NH; 12.4, b, 1H, OH.

36: 3.1–3.3, m,b, 2H, N—CH$_2$; 3.5–3.8, m,b, 6H, N—CH$_2$; 3.48 and 4.51, AB-quartet, J=18.3 Hz, 2H, S—CH$_2$; 5.27, d, J=5.1 Hz, 1H, β-lactam-H; 5.5, m,b, 1H, N—CH; 5.78, d, J=58.3 Hz, 2H, F—CH$_2$; 5.90, dd, J=5.0 Hz and J=8.3 Hz, 1H, β-lactam-H; 6.8–7.0, m, 2H, CH arom.; 7.2–7.4, m, 2H, CH arom.; 8.3, b, NH; 8.62, s, 1H, CH=N; 9.80, d, J=8.3 Hz, 1H, NH; 12.3, b, 1H, OH.

37: 3.48 and 4.55, AB-quartet, J=18.1 Hz, 2H, S—CH$_2$; 3.6, b, 4H, N—CH$_2$; 3.7, b, 4H—CH$_2$; 5.28, d, J=4.9 Hz, 1H, β-lactam-H; 5.6, b, 1H, CH₂F; 5.8–6.0, m, 2H, CH₂F and β-lactam-H; 7.9, b, NH; 8.3, b, NH; 8.64, s, 1H, CH=N; 9.5, b, NH; 9.83, d, J=8,3 Hz, 1H, NH.

38: 1.21, t, 3H, J=7 Hz, CH₃; 2.0–2.2, m, 2H, NCH₂—CH₂—CH₂N; 2.73, s, 3H, H—CH₃; 2.76, s, 3H, N—CH₃; 3.0–3.4, m, 6H, N—CH₂; 3.4–3.7, m, 5H, 4 N—CH₂ and 1 S—CH₂ as part of AB-quartet; 3.57–4.0,m, 4H, N—CH₂; 4.59, 1H as part of AB-quartet of S—CH₂, J=18.2 Hz; 5.31, d, J=5.0 Hz, 1H, β-lactam-H; 5.81, d, J=55 Hz, 2H, CH₂F; 5.95, dd, J=5 Hz and 8.2 Hz, β-lactam-H; 8.7, s, 1H, CH=N; 9.86, d, J=8,2 Hz, 1H, NH.

39: 3.55 and 4.53, AB-quartet, J=18.1 Hz, 2H, S—CH₂; 3.6, b, 4H, N—CH₂; 3.7, b, 4H, N—CH₂; 5.30, d, J=5.1 Hz, 1H, β-lactam-H; 5.88, dd, J=5.1 Hz and J=7.8 Hz, 1H, β-lactam-H; 6.84, s, 1H, CH thiazol; 7.9, b, NH; 8.4, b, NH; 8.70, s, 1H, CH=N; 9.74, d, J=8.0 Hz, 1H, NH; 12.4, b, 2H, OH.

40: 2.3–2.7, m, 4H, C—CH₂; 3.3–3.8, m, 9H, N—CH₂ and S—CH₂, 4.52, part of AB-quartet, J=18.1 Hz, 1H, S—CH₂; 5.31, d, J=5.0 Hz, 1H, β-lactam-H; 5.90, dd, J=5.0 Hz and J=7.8 Hz, 1H, β-lactam-H; 6.83, s, 1H, CH thiazol; 8.3, b, NH; 8.61, s, 1H, CH=N; 9.75, d, J=7.9 Hz, 1H, NH; 12.1, b, 1H, OH; 12.3, b, 1H, OH.

41: 0.6–0.9, m, 4H, CH₂ cycl.; 1.8–2.1, m, 1H, CH cycl.; 3.3–3.9, mb, 9H, N—CH₂ and S—CH₂, 4.52, part of AB-quartet, J=18.0 Hz, 1H, S—CH₂; 5.31, d, J=5.0 Hz, 1H, β-lactam-H; 5.90, dd, J=5.0 Hz and J=7.8 Hz, 1H, β-lactam-H; 6.84, s, 1H, CH thiazol; 8.3, b, NH; 8.63, s, 1H, CH=N; 9.71, d, J=7.9 Hz, 1H, NH; 12.1, b, 1H, OH; 12.3, b, 1H, OH.

42: 3.56 and 4.53, AB-quartet, J=18.2 Hz, 2H, S—CH₂; 3.7, b, 11H, N—CH₂ and O—CH₃; 3.80, s, 6H, O—CH₃; 5.31, d, J=5.0 Hz, 1H, β-lactam-H; 5.90, dd, J=5 Hz and J=7.7 Hz, 1H, β-lactam-H; 6.75, s, 2H, CH arom.; 6.83, s, 1H, CH thiazol; 8.4, b, NH; 8.65, s, 1H, CH=N; 9.76, d, J=7.8 Hz, 1H, NH; 12.3, b, 1H, OH; 12.4, b, 1H, OH.

43: 3.51 and 4.54, AB-quartet, J=18.2 Hz, 2H, S—CH₂; 3.5–3.8, b, 1H, N—CH₂ and O—CH₃; 3.80, s, 6H, O—CH₃; 5.29, d, J=5.0 Hz, 1H, β-lactam-H; 5.65, b, 1H, CH₂F; 5.8–6.0, m, 2H, CH₂F and β-lactam-H; 6.74, s, 2H, CH arom.; 8.3, b, NH; 8.63, s, 1H, CH=N; 9.84, d, J=8.2 Hz, 1H, NH; 12.2, b, 1H, OH/NH.

44: 1.26, d, J=7.2 Hz, 3H, C—CH₃; 3.2–3.7, m b, 9H, N—CH₂ and S—CH₂; 3.9–4.1, m, 1H, N—CH; and 4.27, part of AB-quartet, J=17.5 Hz, 1H, S—CH₂; 5.15, d, J=4.9 Hz, 1H, β-lactam-H; 5.71, dd, J=4.9 Hz and J=7.9 Hz, 1H, β-lactam-H; 6.6, s, 1H, CH thiazol; 7.1, b, NH; 8.59, s, 1H, CH=N; 9.48, d, J=7.9 Hz, 1H, NH; 11.3, b, 1H, OH.

45: 1.23, d, J=7.2 Hz, 3H, C—CH₃; 3.2–3.7, m b, 9H, N—CH₂ and S—CH₂; 3.9–4.1, m, 1H, N—CH; and 4.28, part of AB-quartet, J=17.5 Hz, 1H, S—CH₂; 5.16, d, J=5 Hz, 1H, β-lactam-H; 5.70, dd, J=5 Hz and J=7.9 Hz, 1H, β-lactam-H; 6.7, s, 1H, CH thiazol; 7.1, b, NH; 8.58, s, 1H, CH=N; 9.43, d, J=7.9 Hz, 1H, NH; 11.3, b, 1H, OH.

46: Diastereomer A: 1.26 (d, J=6 Hz, 6H); 1.58 (d, J=5.3 Hz, 3H, —O(CH₃) CH—O—); 2.06 (s, 3H, CH₃CO); 3,5–3,7 (m, 9 H, 8 N—CH₂ and 1 S—CH₂ as part of AB-quartet); 4.4–4.9 (m, 2 H, —O—CH(CH₃)₂ and 1 S—CH₂ as part of AB-quartet); 5,35 (d, J=5,7 Hz, 1H β-lactam-H); 5,81 (d, J=56 Hz, 2H, CH₂F); 6,0 (dd, J=5 and 8,2 Hz, 1H, β-lactam-H); 6,95 (q, 1H, O(CH₃)CH—O—); 8,7 (s, 1H, CH=N), (broad singulet, 2H, NH₂); 9,86 (d, J=8,2 Hz, 1H, NH).

Diastereomer B: 1.26 (d, J=6 Hz, 6H); 1.55 (d, J=5.3 Hz, 3H,—O(CH₃) CH—O—); 2.06 (s, 3H, CH₃CO); 3,5–3,7 (m, 9 H, 8 N—CH₂ and 1 S—CH₂ as part of AB-quartet); 4.4–4.9 (m, 2 H, —O—CH(CH₃)₂ and 1 S—CH₂ as part of AB-quartet); 5,32 (d, J=5,7 Hz, 1H, β-lactam-H); 5,81 (d, J=56 Hz, 2H, CH₂F); 6,0 (dd, J=5 and 8,2 Hz, 1H, β-lactam-H); 6,85 (q, 1H, O(CH₃)CH—O—);8,6 (s, 1H, CH=N); 0,85 (d, J=8,2 Hz, 1H, NH).

47: Diastereomer A: 1.24 (d, J=6 Hz, 6H); 1.53 (d, J=5.4 Hz, 3H, —O(CH₃) CH—O—); 3.88 (broad singulet, 4H); 4.0 (boad singulet, 4H); 4.10 (AB-quartet, J=18.4 Hz, S—CH₂); 4.78 (q, 1H, —O—CH(CH₃)₂); 5.3 (d, J=5.1 Hz, 1H, β-lactam-H); 5.78 (d, J=55 Hz, 2H, CH₂F); 5.96 (dd, J=5.1 and 8.4 Hz, 1H, β-lactam-H); 6.81 (q, 1H, O(CH₃)CH—O—); 8.0 (s, 1H, CH=N); (broad singulet, 2H, NH2); 9.79 (d, J=8,4 Hz, 1H, NH).

Diastereomer B: 1.25 (d, J=6 Hz, 6H); 1.56 (d, J=5.4 Hz, 3H, —O(CH₃) CH—O—); 3.88 (broad singulet, 4H); 4.0 (broad singulet, 4H); 4.11 (AB-quartet, J=18.4 Hz, S—CH₂); 4.80 (q, 1H, —O—CH(CH₃)₂); 5.33 (d, J=5.1 Hz, 1H, β-lactam-H); 5.78 (d, J=55 Hz, 2H, CH₂F); 5.99 (dd, J=5.1 and 8.4 Hz, 1H, β-lactam-H); 6.92 (q, 1H, O(CH₃) CH—O—); 8.7 (s, 1H, CH=N): 9.81 (d, J=8.4 Hz, 1H, NH).

48: Diastereomer A: 1.25, d, J=6.2 Hz, 6H; 1.53, d, J=5.3 Hz, 3H, —O(CH₃) CH—O—; 2.08 s, 3H, CH₃CO; 3.1–3.3, m, 2H, N—CH₂; 3,5–3,7, m, 9 H, 8 N—CH₂ and 1 S—CH₂; as part of AB-quartet; 4.5–4.9, m, 2 H, —O—CH(CH₃)₂ and 1 S—CH₂ as part of AB-quartet; 5,31, d, J=5,5 Hz, 1H, β-lactam-H; 5,80, d, J=55 Hz, 2H, CH₂F; 5.98, dd, J=5 and 8.5, 2H, 1H, β-lactam-H; 6,7–7, 0, m, 3H, O(CH₃)CH—O— and 2 CH aromat.; 7,32, d, J=8.5, 2H, CH arom.; 8.59, s, 1H, CH=N; 9,84, d, J=8,3 Hz, 1H, NH.

Diastereomer B: 1.25, d, J=6 Hz, 6H; 1.57, d, J=5.3 Hz, 3H, —O(CH₃)CH—O—; 2.09, s, 3H, CH₃CO; 3.1–3.3, m, 2H, N—CH₂; 3,5–3,7, m, 9 H, 8 N—CH₂ and 1 S—CH₂ as part of AB-quartet; 4.5–4.9, m, 2 H, —O—CH(CH₃)₂ and 1 S—CH₂ as part of AB-quartet; 5,34, d, J=5,8 Hz, 1H, β-lactam-H; 5,80, d, J=55 Hz, 2H, CH₂F; 5,98, dd, J=5 and 8,2 Hz, 1H, β-lactam-H; 6,7–7,0, m, 3H, O(CH₃)CH—O— and 2 CH aromat.; 7,32, d, J 8.5, 2H, CH arom.; 8,69, s, 1H, CH=N; 9.85, d, J=8,2 Hz, 1H, NH.

49: Diastereomer A: 1.16, s, 9H, C—CH₃; 3.46 and 3.92, AB-quartet, J=18.0 Hz, S—CH₂; 5.33, d, J=5.3 Hz, 1H, β-lactam-H; 5.78, d, J=55 Hz, 2H, CH₂F; 5.90 and 5.98, AB-quartet, J=6.04 Hz, OCH₂O—; 6.06, dd, J=5.3 and 8.3 Hz, 1H, β-lactam-H; 8.2, broad singulet, 2H, NH₂; 9.65, s, 1H, CH=O; 9.88, d, J=8,3 Hz, 1H, NH.

Diastereomer B: 1.18, s, 9H, C—CH₃; 3.1–3.3, m, 2H, N—CH₂; 3.4–3.8, m, 6H, N—CH₂; 3.5 and 4.65, AB-quartet, J=18.5 Hz, S—CH₂; 5.34, d, J=5.0 Hz, 1H, β-lactam-H; 5.66, m, 1H, N—CH; 5.79, d, J=55 Hz, 2H, CH₂F; 5.7–6.0, m, 3H, OCH₂O— and β-lactam-H; 6.88 and 7.32, d and d, J=8.4 and J=8.5, 4H, CH arom.; 8.75, s, 1H, CH=N; 9.87, d, J=8,2 Hz, 1H, NH.

Aa: 2,55 (s, 3H, S—CH₃); 3,45 (s, 3H, N—CH₃).

Ab: 3,4 (s, 3H, N—CH₃); 3,51 (m, 2H) and 3,58 (m, 6H, —CH₂—N—CH₂—); 7,45–7,48 (m, 3H, CH arom.); 7,81–7,85 (m, 2H, CH arom.); 8,10 (s, 1H, N—CH=O); 8,14 (s, 1H, CH=N); 9,0 (broad singulet, 2H, N⁺H₂).

Ac: 3,16 (m, 7H, N—CH₃ and —CH₂—N—CH₂—); 3,61 (m, 4H, —CH₂—N⁺—CH₂—); 6.0 (broad singulet, 3H, N⁺H₃); 8,3 (broad singulet, 1H, NH); 10.0 (broad singulet, 2H, N⁺H₂).

B: 1.22, t, J=5 Hz, 3H, CH₃; 3.16, b, 4H, N—CH₂; 3.45, q, J=5 Hz, 2H, CH₂; 3.65, b, 4H, N—CH₂; 10.14, b, 2H, NH.

C: 3.14, b, 4H, N—CH₂; 3.68, b, 4H, N—CH₂; 3.98–4.18, m, 2H, CH₂—C; 5.16–5.48, m, 2H, CH₂=C; 5.80–6.10, m, 1H, CH=C; 10.30, b, 2H, NH.

D: 3.19, b, 4H, N—CH$_2$; 3.67, b, 4H, N—CH$_2$; 3.77, s, 3H, O—CH$_3$; 4.59, s, 2N—CH$_2$; 6.90–7.02 and 7.25–7.38, m, each 2H, CH-arom.; 10.02, b, 2H, NH.

E: 3.20, b, 4H, N—CH$_2$; 3.67, b, 7H, 4H of N—CH$_2$ and 3H of O—CH$_3$; 3.81, s, 6H, O—CH$_3$; 4.59, s, 2H, N—CH$_2$; 6.69, s, 2H, CH-arom.; 9.96, b, 2H, NH.

F: 2.84, s, 3H, CH$_3$; 3.18, b, 7H, 4H of N—CH$_2$ and 3H of CH$_3$; 3.63, b, 4H, N—CH$_2$; 10.13, b, 2H, NH.

G: 1.20, t, J=5 Hz, 3H, CH$_3$; 3.19, b, 9H, 4H of N—CH$_2$ and 3H of CH$_3$ and 2H of CH$_2$; 3.64, b, 4H, N—CH$_2$; 10.12, b, 2H, NH.

La: 3.32 and 3.70 (AB Quartet, J=17 Hz, 2H, SCH$_2$); 5.22 (d, J=5 Hz, 1H, β-lactam-H); 5.82 (d, J=55 Hz, 2H, CH$_2$F); 5.86 (dd, J=5 and 8,4 Hz, 1H, β-lactam-H); 8.35 (broad singulet, 2H, NH$_2$); 9.5 (s, 1H, CH=O); 9.88 (d, J=8,4 Hz, 1H, NH).

Lb: Diastereomer A: 1.21 (d, J=6 Hz, 6H); 1.53 (d, J=5.4 Hz, 3H, —O(CH$_3$)CH—O—); 3.67 (AB-quartet, J=18.2 Hz, S—CH$_2$); 4.64.9 (m, 2 H, —O—CH(CH$_3$)$_2$; 5.32 (d, J=5.3 Hz, 1H, β-lactam-H); 5.8 (d, J=55 Hz, 2H, CH$_2$F); 6.04 (dd, J=5.3 and 8.4 Hz, 1H, β-lactam-H); 6.84 (q, 1H, O(CH$_3$)CH—O—); 8.2 (broad singulet, 2H, NH2); 9.6 (s, 1H, CH=O); (broad singulet, 2H, NH2); 9.88 (d, J=8,4 Hz, 1H, NH).

Diastereomer B: 1.23 (d, J=6 Hz, 6H); 1.53 (d, J=5.4 Hz, 3H, —O(CH$_3$)CH—O—); 3.68 (AB-quartet, J=18.2 Hz, S—CH$_2$); 4.6–4.9 (m, 1H, —O—CH(CH$_3$)$_2$; 5.33 (d, J=5.3 Hz, 1H, β-lactam-H); 5.8 (d, J=55 Hz, 2H, CH$_2$F); 6.08 (dd, J=5.3 and 8.4 Hz, 1H, β-lactam H); 6.93 (q, 1H, O(CH$_3$)CH—O—); 9.6 (s, 1H, CH=O): 9.88 (d, J 8.4 Hz, 1H, NH).

What is claimed is:

1. A compound of formula

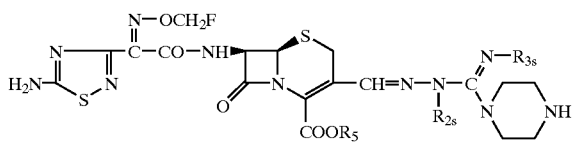

Is wherein

R$_5$ denotes hydrogen or an ester moiety;

R$_{2S}$ denotes (C$_{1-8}$)alkyl; and R$_{3S}$ denotes hydrogen, (C$_{1-8}$)alkyl, (C2–8)alkenyl or (C3–8)cycloalkyl, in free form or in form of a salt or in form of a solvate.

2. A compound according to claim 1 wherein R$_{2S}$ is methyl and R$_{3S}$ is hydrogen.

3. (((5-Amino-1,2,4-thiadiazol-3-yl)-(Z)-(fluoromethoxyimino)acetyl)amino)-3(E)-((imino-1-piperazinylmethyl) methylhydrazono)methyl-3-cephem-4-carboxylic acid in the form of a hydrochloride.

4. 7-(((5-Amino-1,2,4-thiadiazol-3-yl)-(Z)-(fluoromethoxyimino)acetyl)amino)-3-(E)((imino-1-piperazinylmethyl) methylhydrazono)methyl-3-cephem-4-carboxylic acid in the form of a trihydrochloride.

5. A process for the production of a compound of formula Is, as defined in claim 1, comprising a) reacting a compound of formula

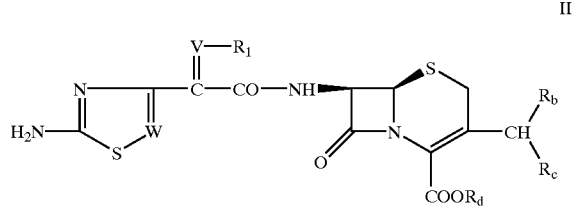

II wherein W is N, V is N—O and R$_1$ denotes CH$_2$F and wherein either

α) R$_b$ denotes hydroxy and R$_c$ and R$_d$ together denote a bond, or

β) R$_d$ denotes hydrogen, a cation, an ester moiety or a silyl protecting group and R$_b$ and R$_c$ together denote the oxo group with a compound of formula

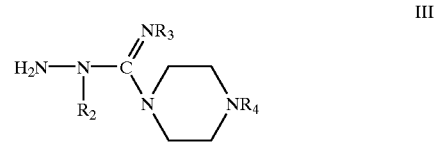

III wherein R$_4$ is hydrogen and R$_2$ and R$_3$ are as defined as in claim 1 and isolating a compound of formula Is.

6. A pharmaceutical composition comprising a compound of formula Is as defined in claim 1 in the form of a pharmaceutically acceptable salt or in free form in association with at least one pharmaceutical carrier or diluent.

7. A method of treatment of bacterial diseases which comprises administering to a subject in need of such treatment an effective amount of a compound of formula Is as defined in claim 1.

* * * * *